(12) United States Patent
Lin et al.

(10) Patent No.: US 10,955,400 B2
(45) Date of Patent: Mar. 23, 2021

(54) DRINKING WATER HEAVY METALS SENSOR AND METHODS FOR USE THEREOF

(71) Applicant: THE REGENTS OF THE UNIVERSITY OF MICHIGAN, Ann Arbor, MI (US)

(72) Inventors: Wen-Chi Lin, Ypsilanti, MI (US); Mark A. Burns, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 178 days.

(21) Appl. No.: 15/986,389

(22) Filed: May 22, 2018

(65) Prior Publication Data
US 2018/0335415 A1 Nov. 22, 2018

Related U.S. Application Data

(60) Provisional application No. 62/509,537, filed on May 22, 2017.

(51) Int. Cl.
*G01N 33/18* (2006.01)
*G01N 27/12* (2006.01)
*G01N 27/07* (2006.01)

(52) U.S. Cl.
CPC .......... *G01N 33/1813* (2013.01); *G01N 27/07* (2013.01); *G01N 27/12* (2013.01)

(58) Field of Classification Search
CPC .... G01N 33/1813; G01N 27/07; G01N 27/12; G01N 27/267; H01L 51/0575; H01L 51/105; H01L 51/0022; H01L 51/0004; B82Y 15/00
See application file for complete search history.

(56) References Cited

U.S. PATENT DOCUMENTS

| | | | |
|---|---|---|---|
| 5,437,772 | A | 8/1995 | De Castro et al. |
| 6,110,354 | A | 8/2000 | Saban et al. |
| 8,128,794 | B2 | 3/2012 | Rhee et al. |
| 2001/0042693 | A1 | 11/2001 | Onitskansky |
| 2003/0155241 | A1 | 8/2003 | Lai et al. |

(Continued)

FOREIGN PATENT DOCUMENTS

WO    WO-2013141692 A1    9/2013

OTHER PUBLICATIONS

International Preliminary Report on Patentability in corresponding PCT Application No. PCT/US2018/033931, dated Nov. 26, 2019, 12 pages.

(Continued)

*Primary Examiner* — Suman K Nath
(74) *Attorney, Agent, or Firm* — Lempia Summerfield Katz LLC

(57) ABSTRACT

A sensor for detecting heavy metals in water is provided. The sensor includes a first electrode and a second electrode, the first electrode and the second electrode having complementary interdigitated surfaces that are separated from each other by a first gap having a distance of greater than or equal to about 500 nm to less than or equal to about 10 μm. The sensor also includes a power source connectable to the first electrode and the second electrode. The sensor is configured to continuously monitor water for the presence of heavy metals. Methods of making and using the sensor are also provided.

22 Claims, 13 Drawing Sheets

(56) References Cited

U.S. PATENT DOCUMENTS

| | | | |
|---|---|---|---|
| 2011/0308942 A1 | 12/2011 | Liu et al. | |
| 2016/0238583 A1* | 8/2016 | Kodzius | G01N 33/24 |
| 2017/0328941 A1* | 11/2017 | Atashbar | H01L 51/0575 |

OTHER PUBLICATIONS

International Search Report and Written Opinion for PCT/US2018/033931, dated Sep. 11, 2018; ISA/KR.

Abbaspour, Abdolkarim et al., "Platinum electrode coated with a bentonite-carbon composite as an environmental sensor for detection of lead." Analytical and Bioanalytical Chemistry, vol. 386, 2006, pp. 1559-1565.

Amazon.com, Inc. "WaterSafe Water Test Kit for Lead by Watersafe." Water Test Kits, https://www.amazon.com/WaterSafe-Water-Test-Kit-Lead/dp/B000Q6QWZA.

Aragay, Gemma et al., "Enhanced electrochemical detection of heavy metals at heated graphite nanoparticle-based screen-printed electrodes." Journal of Materials Chemistry, The Royal Society of Chemistry, vol. 21, 2011, pp. 4326-4331.

Cankurtaran, Hüsnü et al., "Conductive composites of serigraphic inks and their usage in heavy metal sensor and biosensor." Progress in Organic Coatings, vol. 98, 2016, pp. 6-9.

El Mhammedi, M.A. et al., "Evaluation of a platinum electrode modified with hydroxyapatite in the lead(II) determination in a square wave voltammetric procedure." Arabian Journal of Chemistry, King Saud University, vol. 6, 2013, pp. 299-305.

Gumpu, Manju Bhargavi et al. "A review on detection of heavy metal ions in water—An electrochemical approach." Sensors and Actuators B: Chemical, vol. 213, 2015, pp. 51-533.

Hamer, M. et al., "Polyallylamine-chlorophyllide derivatized gold and silver nanoparticles as optical probes for sensor applications." Sensors and Actuators B, vol. 145, No. 1, 2010, pp. 250-253.

Inlet Innovations, Inc., "Water Test Kits." Test Assured Water Testing Kits and Supplies, 2016, https://watertestingkits.com/product-category/water-test-kits/.

Ly, SuwYoung et al., "Real-time Assay of Toxic Lead in In Vivo Living Plant Tissue." Toxicological Research, vol. 29, No. 4, 2013, pp. 293-298.

NanoAffix Science, LLC, "Platform Technology." 2016, http://www.nanoaffix.com/platform.html.

Sarkar, Sahana et al., "Redox cycling without reference electrodes." Analyst, The Royal Society of Chemistry, vol. 139, 2014, pp. 6052-6057.

United States Environmental Protection Agency, "Final Report: Advanced Nanosensors for Continuous Monitoring of Heavy Metals." EPA Grant No. R830906, 2006, https://cfpub.epa.gov/ncer_abstracts/index.cfm/fuseaction/display.highlight/abstract/6124/report/F.

Vlascici, Dana et al., "Free Base Porphyrins as Ionophores for Heavy Metal Sensors." Sensors, vol. 8, 2008, pp. 4995-5004.

Xuan, Xing et al. "A Fully Integrated and Miniaturized Heavy-metal-detection Sensor Based on Micro-patterned Reduced Graphene Oxide." Scientific Reports, Nature, vol. 6, No. 33125, 2016.

Extended European Search Report in European Patent Application No. 18805513, dated Feb. 4, 2021, 12 pages.

* cited by examiner

FIG. 3A  FIG. 3B

100 ml test solution aA-Bb : Electroplating mode
aA-BB' : ΔV$_1$ (Lead sensor)
A'A-Bb : ΔV$_2$ (Other metal sensor)

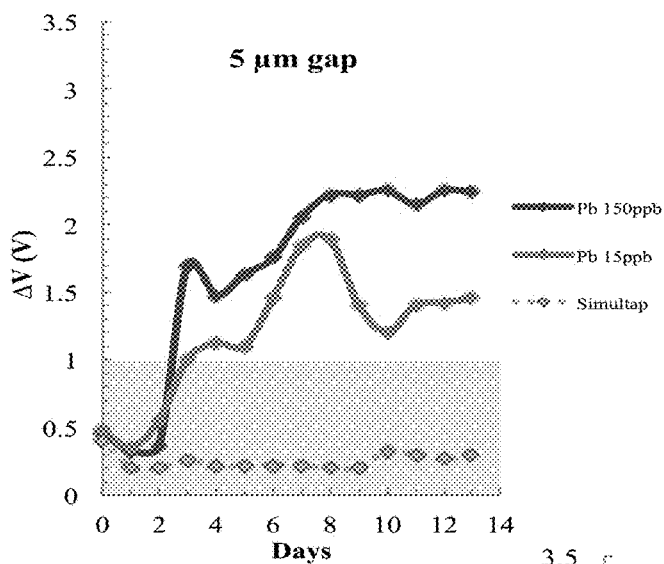
FIG. 5A
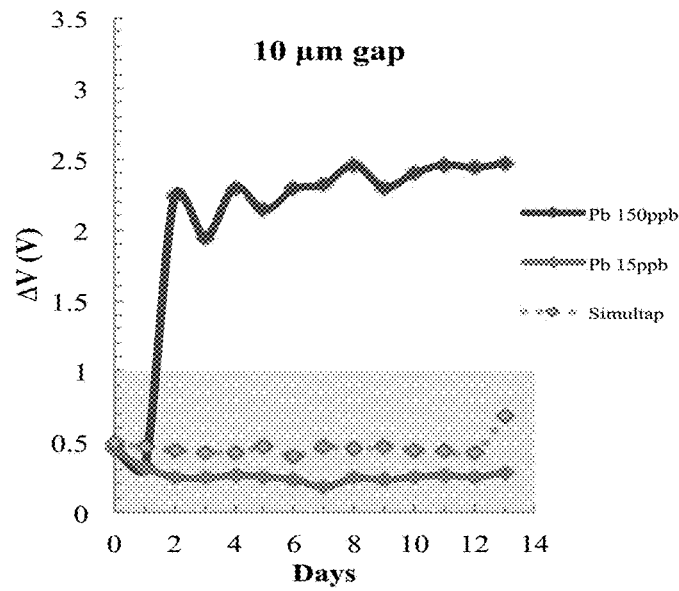
FIG. 5B
FIG. 5C
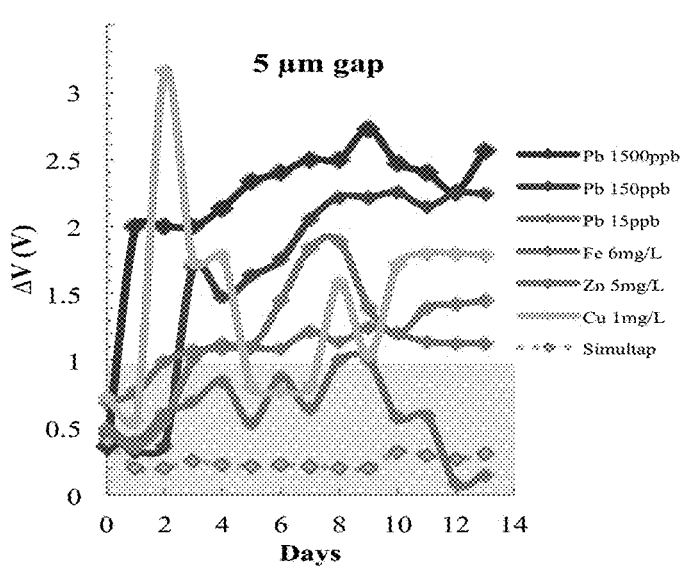

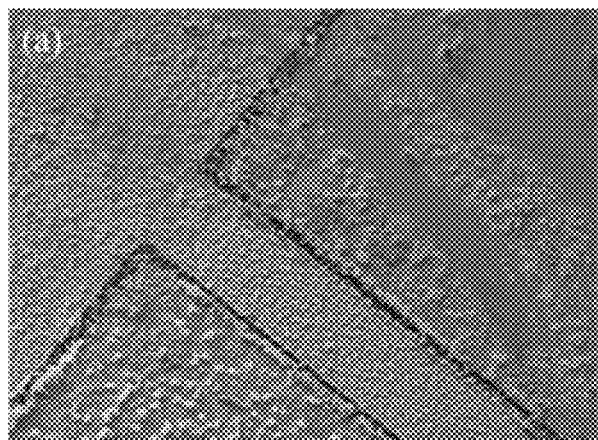
FIG. 11A
FIG. 11B
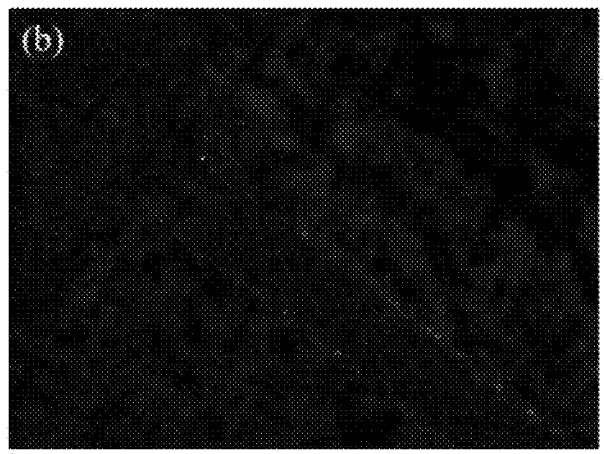
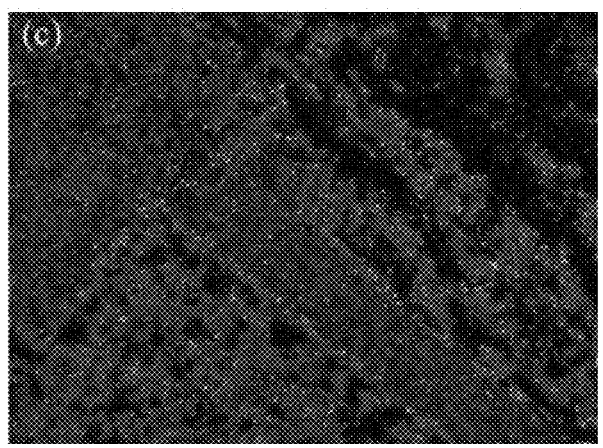
FIG. 11C

Add more sensors if necessary

...and repeat

DRINKING WATER HEAVY METALS SENSOR AND METHODS FOR USE THEREOF

CROSS-REFERENCE TO RELATED APPLICATIONS

This application claims the benefit of U.S. Provisional Application No. 62/509,537, filed on May 22, 2017. The entire disclosure of the above application is incorporated herein by reference.

FIELD

The present disclosure relates to sensors that monitor home water for heavy metals, such as lead.

BACKGROUND

This section provides background information related to the present disclosure which is not necessarily prior art.

Heavy metals, such as lead, in drinking water are dangerous to humans, and regulations for the maximum allowable concentrations of these metals in drinking water have been established to protect consumers. Lead causes neurological damage even at low levels of lead exposure, especially in infants and children. The Environmental Protection Agency (EPA) states that zero lead is allowed in maximum contaminant level (MCL), and 15 ppb of lead is listed as the action level. In addition to lead, copper is another dangerous heavy metal that causes liver and kidney damage after long-term exposure. The MCL for copper is 1.3 mg/L and the secondary maximum contaminant levels (SMCL) is 1.0 mg/L. SMCLs suggest ions that cause bad taste, color, and odor should be minimized in drinking water. Zinc and iron are other two common elements in drinking water that are regulated by SMCLs of 5 mg/L and 0.3 mg/L, respectively.

Lead leakage into tap water is a major concern in the U.S. Houses in the U.S. built before 1986 commonly contain lead in the service lines or valves. When water flows through these lead components, lead can leach into the water through a variety of complex electrochemical, geochemical, and hydraulic mechanisms. The leaching often occurs without the awareness of the users because lead can be colorless and odorless. Thus users are at risk from lead exposure through contaminated water if the metal contaminant is not detected.

Early detection of lead is important to prevent long-term exposure, but is difficult to achieve using current technology. Because water is contaminated inside the structure of a house, end-point detection by home-monitoring is crucial for lead leakage detection. The only qualified method suggested by EPA is inductively coupled plasma mass spectrometry (ICPMS) at qualified national testing labs. Because lead leakage typically happens unexpectedly, the suggested method requires the self-awareness of the users to regularly send water out for examination. Although minimized sensors for home-monitoring have been proposed using electrochemical potentialmetric or colorimetric methods, most potentialmetric sensors have short lifetimes due to the limitation of minimized reference electrodes, and colorimetric sensors are typically single use. Accordingly, there remains a strong need to develop sensors that detect metals in water and that can operate for a long time without input from a user.

SUMMARY

This section provides a general summary of the disclosure, and is not a comprehensive disclosure of its full scope or all of its features.

The current technology provides a sensor for detecting heavy metals in water. The sensor includes a first electrode and a second electrode, the first electrode and the second electrode having complementary interdigitated surfaces that are separated from each other by a first gap having a distance of greater than or equal to about 500 nm to less than or equal to about 10 µm; and a power source connectable to the first electrode and the second electrode. The sensor is configured to continuously monitor water for the presence of heavy metals.

In one various, the first electrode is a positive electrode and the second electrode is a negative electrode.

In one variation, the first electrode has a surface area of greater than or equal to about 0.4 $mm^2$ to less than or equal to about 0.5 $mm^2$ and the second electrode has a surface area of greater than or equal to about 0.3 $mm^2$ to less than or equal to about 0.4 $mm^2$.

In one variation, the sensor further includes a third electrode and a fourth electrode, the third electrode and the fourth electrode having complementary interdigitated surfaces that are separated from each other by a distance of greater than or equal to about 500 nm to less than or equal to about 10 µm. The second electrode and the third electrode are separated from each other by a second gap having a distance of greater than or equal to about 1 µm to less than or equal to about 1 mm.

In one variation, the first electrode is a positive electrode and the fourth electrode is a negative electrode.

In one variation, the sensor further includes a first lead electrically connected to the first electrode; a second lead electrically connected to the second electrode; a third lead electrically connected to the third electrode; and a fourth lead electrically connected to the fourth electrode, wherein the sensor is configured such that the first, second, third and fourth leads can be individually coupled to and decoupled from the power source.

In one variation, the power source is a battery, a plurality of batteries, a photovoltaic device, or an electrical service of a building.

In one variation, the sensor continuously and selectively detects lead in water.

In one variation, the sensor is free of a reference electrode and a ligand.

In one variation, the sensor also includes a substrate portion coupled to the first and second electrodes by way of an adhesive layer disposed between the substrate portion and the first and second electrodes.

In one variation, a water pipe having an internal bore section through which water flows, wherein the sensor is disposed within the internal bore section, is provided.

The current technology also provides a method of continuously monitoring water for the presence of lead. The method includes contacting a sensor with a water sample. The sensor includes a first electrode and a second electrode, the first electrode and the second electrode having complementary surfaces that are separated from each other by a distance of greater than or equal to about 500 nm to less than or equal to about 10 µm; a third electrode and a fourth electrode, the third electrode and the fourth electrode having complementary surfaces that are separated from each other by a distance of greater than or equal to about 500 nm to less than or equal to about 10 µm, wherein the second electrode and the third electrode are separated from each other by a distance of greater than or equal to about 1 µm to less than or equal to about 1 mm. The method also includes applying a first electrical potential between the first and fourth electrodes; applying a second electrical potential between the first and second electrodes; measuring a first voltage between the first and second electrodes; and determining that lead is present in the water sample when comparing the first voltage to a baseline voltage in water that does not contain detectable levels of lead.

In one variation, the water sample is contained in a water pipe.

In one variation, the method further includes generating an alert when the first voltage is different from the baseline voltage.

In one variation, the method further includes, after the measuring a voltage between the first and second electrodes, applying a third electrical potential between the third and fourth electrodes; measuring a second voltage between the third and fourth electrodes; and determining that heavy metals other than lead are present in the water when comparing the second voltage to second baseline voltage in water that does not contain detectable levels of heavy metals other than lead.

In one variation, the sensor is free of a reference electrode or a ligand.

The current technology also includes a method of fabricating an electrode that selectively detects lead in water. The method includes disposing an adhesive layer on a substrate; disposing a photoresist onto the adhesive layer; and disposing a photoresist mask on the photoresist, wherein the photoresist mask includes a pattern. The pattern defines a first electrode and a second electrode, the first electrode and the second electrode having complementary surfaces that are separated from each other by a distance of greater than or equal to about 500 nm to less than or equal to about 10 µm; and a third electrode and a fourth electrode, the third electrode and the fourth electrode having complementary surfaces that are separated from each other by a distance of greater than or equal to about 500 nm to less than or equal to about 10 µm, wherein the second electrode and the third electrode are separated from each other by a distance of greater than or equal to about 1 µm to less than or equal to about 1 mm. The method also includes transferring the pattern of the photoresist mask into the adhesive layer to generate a patterned adhesive layer; and disposing a layer of a conductive material onto the patterned adhesive layer.

In one variation, the adhesive layer includes titanium, platinum, or a combination thereof.

In one variation, the conductive material includes platinum, gold, silver, copper, or a combination thereof.

In one variation, the substrate includes silicon dioxide.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 3C:
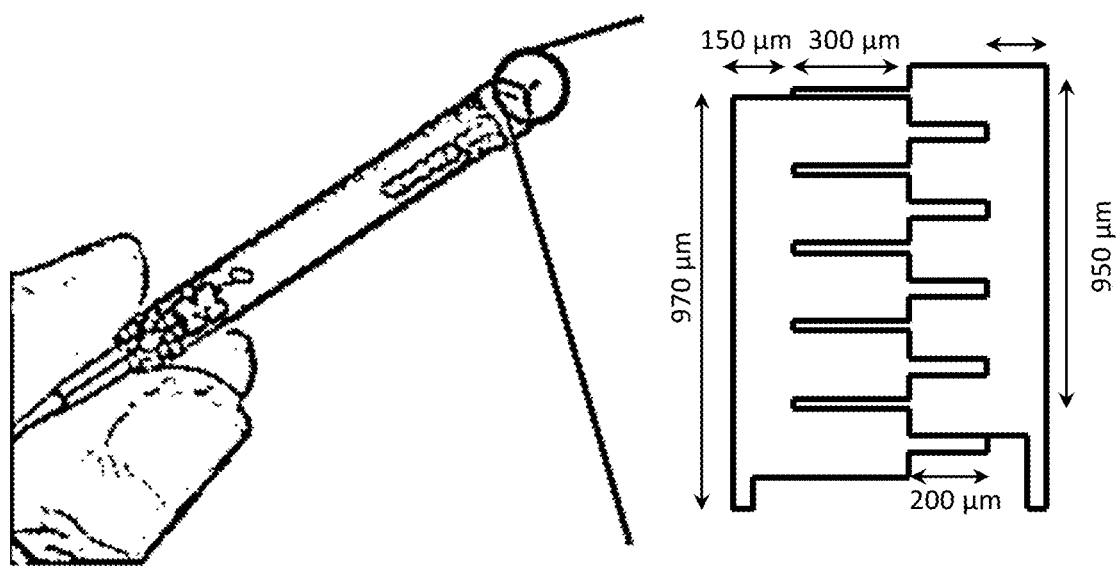
FIG. 3A is a photograph of an exemplary two-electrode sensor.
FIG. 3B is an illustration of the two-electrode sensor shown in FIG. 3A.
Figure 3C:
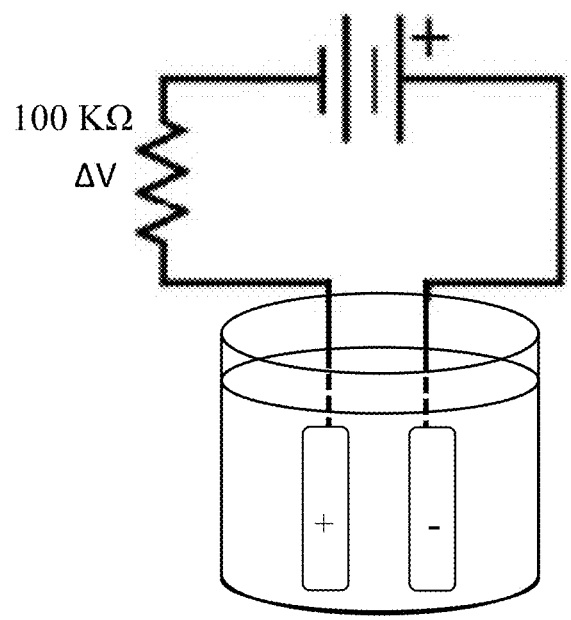

FIG. 3C is a schematic of a system of detecting heavy metals in water with the two-electrode sensor shown in FIGS. 3A and 3B. The sensor was immersed in 100 ml test solution and connected with two AAA batteries and a 100 kΩ resistor. Voltage across the resistor, $\Delta V$, was measured as the sensor output.

Figure 4A:
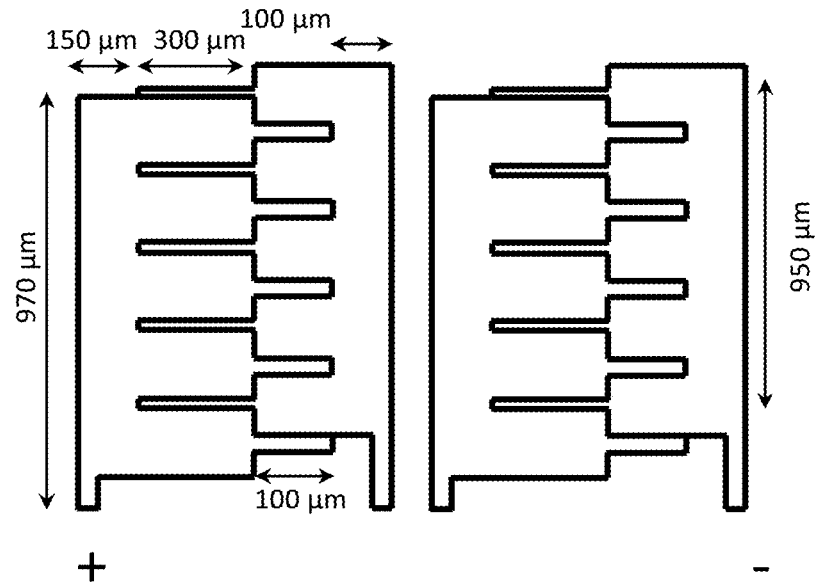

FIG. 4A is an illustration of a four-electrode sensor geometry according to various aspects of the current technology.

Figure 4B:
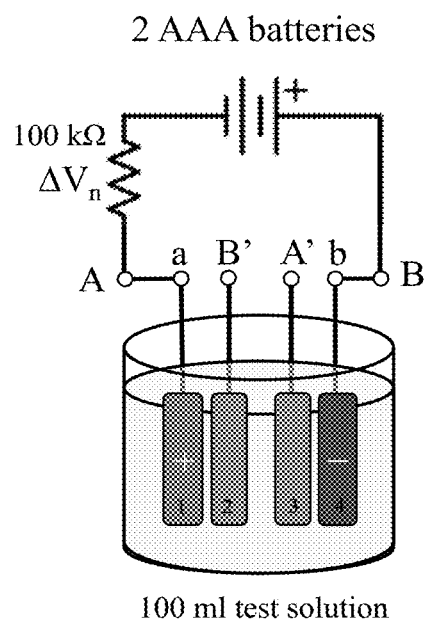

FIG. 4B is a schematic of a system of detecting heavy metals in water with the four-electrode sensor shown in FIG. 4A. The sensor was immersed in 100 ml test solution and connected as aA-Bb when it was operated. Voltage across the resistor was measured as $\Delta V_1$ when connected as aA-BB' and as $\Delta V_2$ when A'A-Bb.

FIG. 5A is a reading of $\Delta V$ from a two-electrode sensor with 5 µm gap.

FIG. 5B is a reading of $\Delta V$ from a two-electrode sensor with 10 µm gap.

FIG. 5C shows $\Delta V$ readings from a two-electrode sensor having a 5 µm gap in various simulated solutions.

Figure 6:
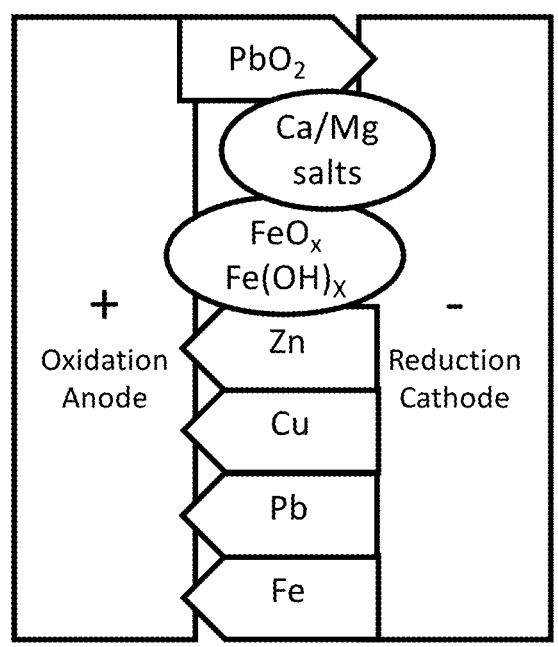

FIG. 6 is an illustration showing that in a two-electrode system according to various aspects of the current technology, where metals reduce or oxidize into conductive species (drawn as arrows). Some nonconductive salts and rust (drawn as circles) also precipitate on the sensor.

Figure 7:
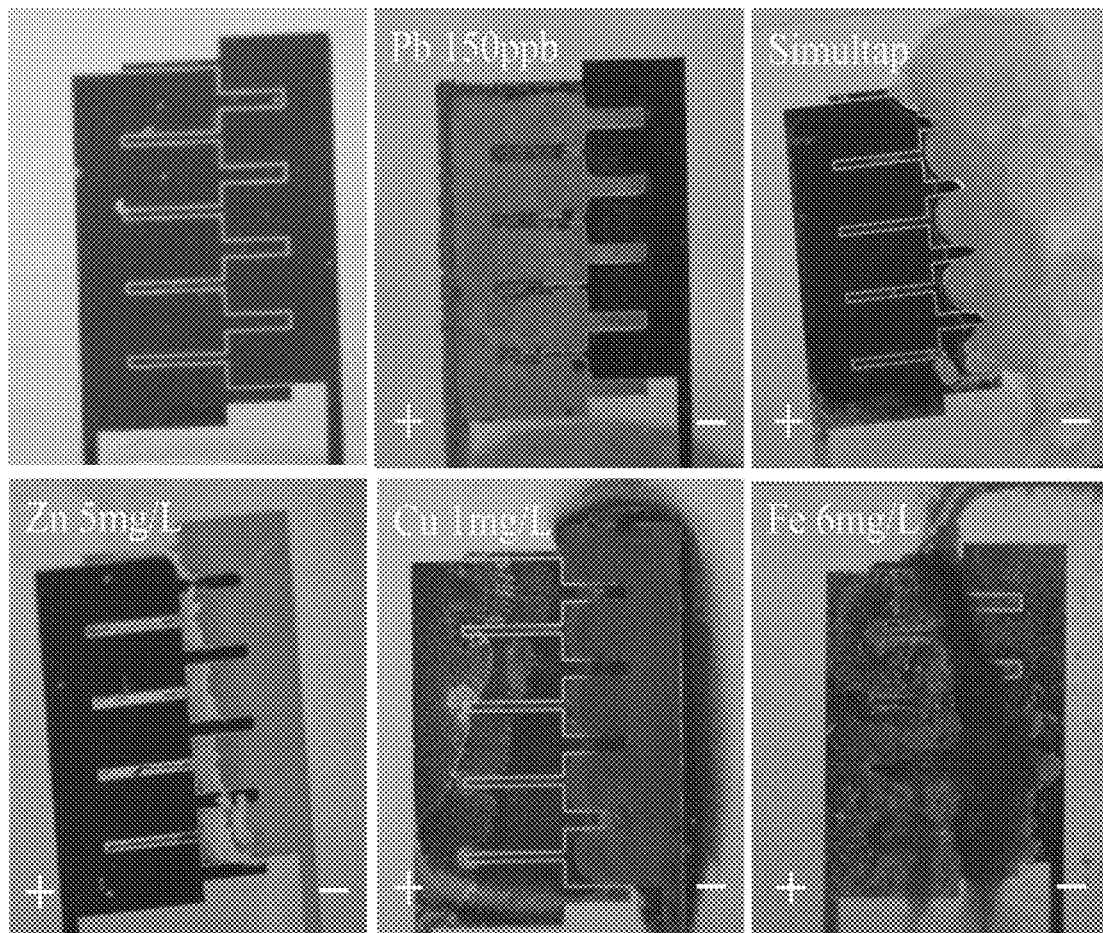

FIG. 7 shows photographs of an exemplary two-electrode sensor (top left) before and after it is operated in various solutions for two weeks. Lead deposits on an anode while all other metals deposit or precipitate on the cathode.

Figure 8:
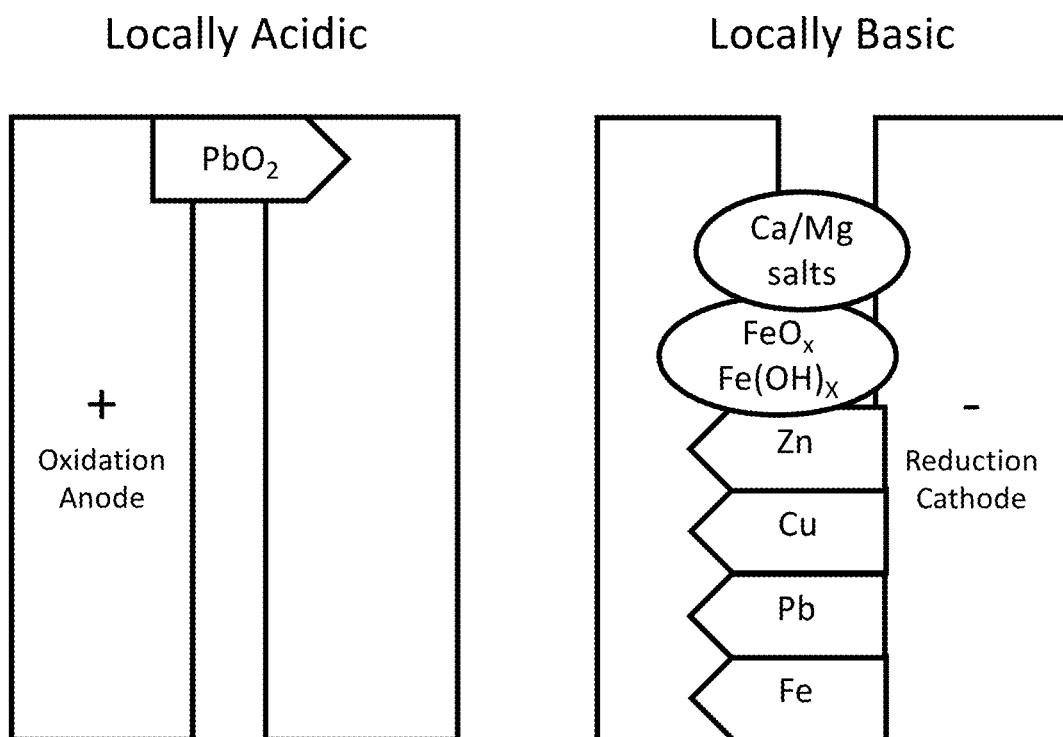

FIG. 8 is an illustration showing that in a four-electrode system, lead is oxidized to conductive lead dioxide on an anode, and other metals are reduced to conductive species (drawn as arrows) on a cathode. Nonconductive salts and rust (drawn as circles) also precipitate on the cathode.

Figure 9A:
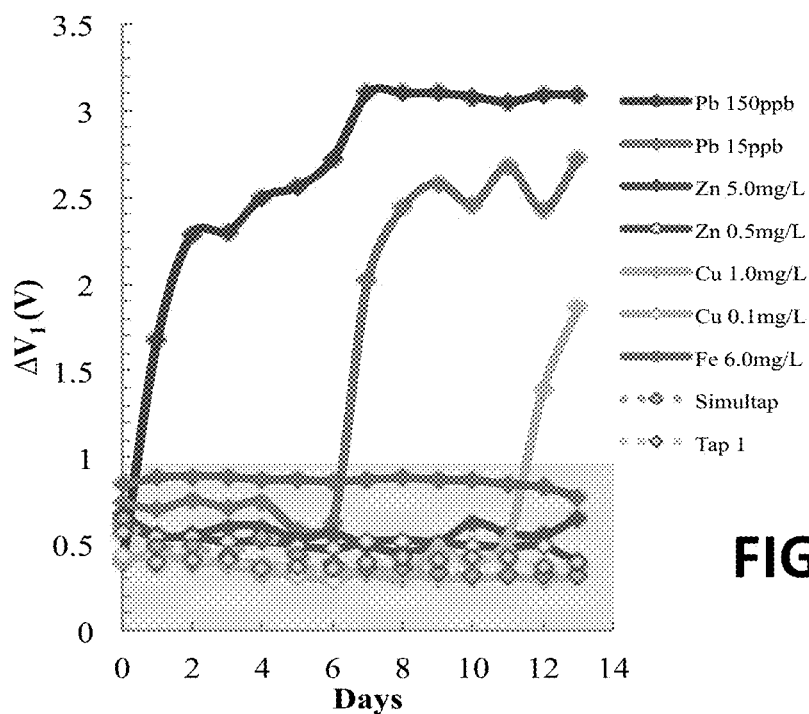

FIG. 9A shows an original $\Delta V_1$ reading at an anode of an exemplary four-electrode sensor.

Figure 9B:
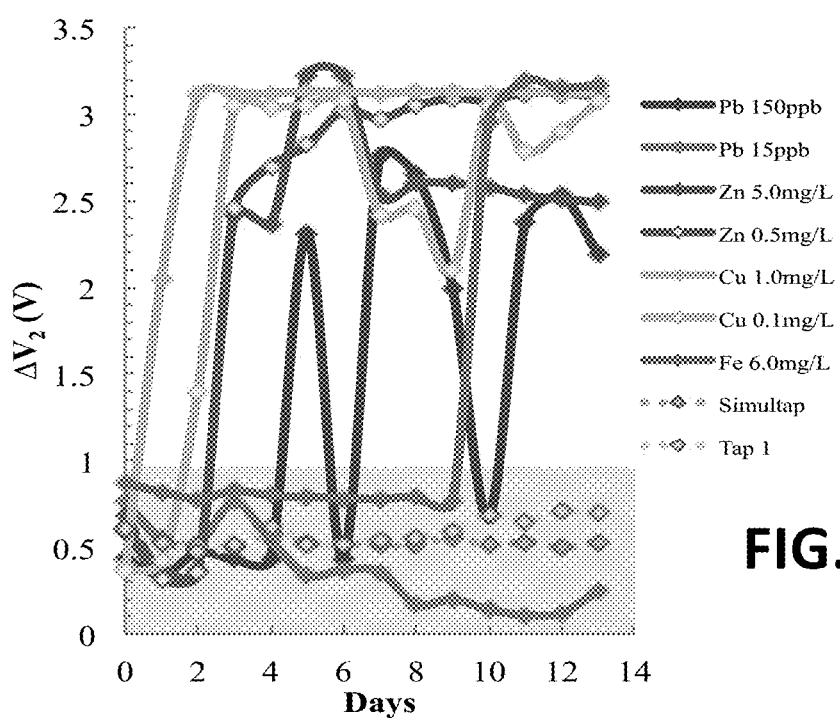

FIG. 9B shows an original $\Delta V_2$ reading at a cathode of an exemplary four-electrode sensor disposed in different solutions for two weeks.

Figure 10A:
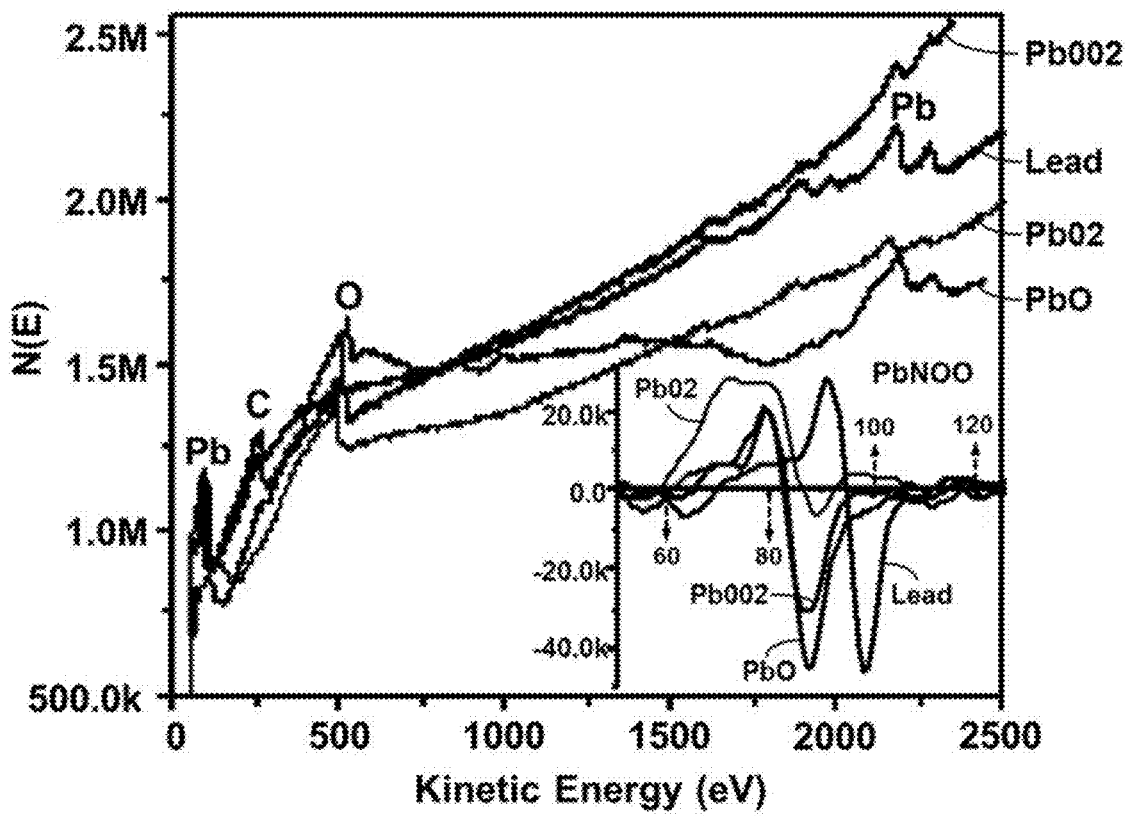

FIG. 10A shows Auger electron spectra of standard metal lead, standard lead (II) oxide, sample Pb02 (150 ppb Pb) and Pb002 (15 ppb Pb). The inset expands the Pb N00 Auger transitions in a first order derivative.

Figure 10B:
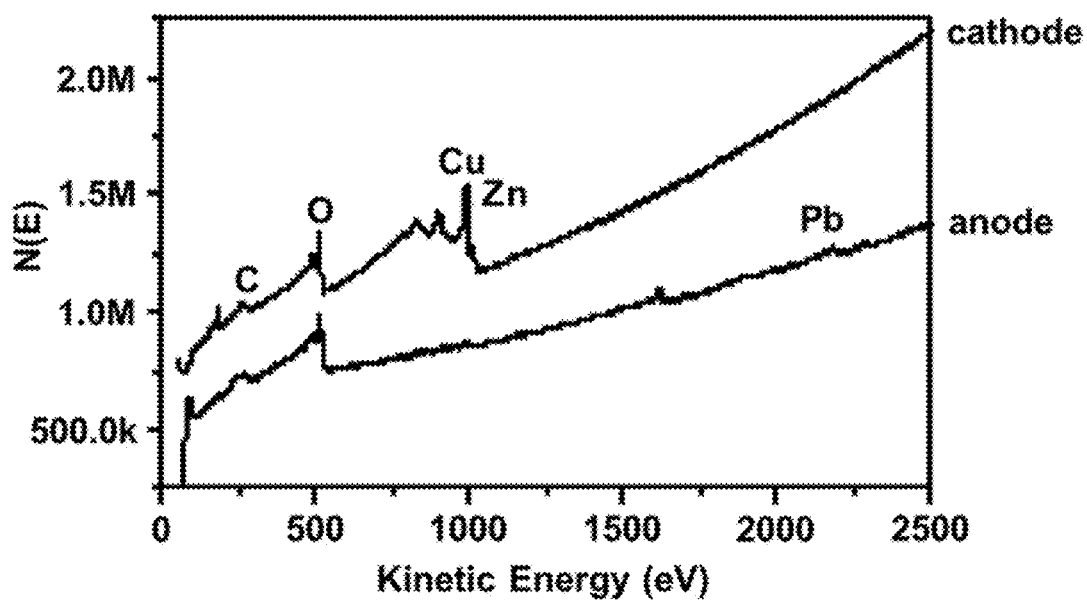

FIG. 10B shows Auger electron spectra profiles of an anode and a cathode of a sample having "Pb 15 ppb+Cu 1 mg/L+Zn 5 mg/L."

FIG. 11A is a scanning electron microscopy image and electron mapping at Pb transition peaks from a Pb02 sample under an electronic impact of 10 kV and 10 nA.

FIG. 11B is a scanning electron microscopy image and electron mapping at NOO transition peaks from a Pb02 sample under an electronic impact of 10 kV and 10 nA.

FIG. 11C is a scanning electron microscopy image and electron mapping at MNV transition peaks from a Pb02 sample under an electronic impact of 10 kV and 10 nA.

Figure 12A:
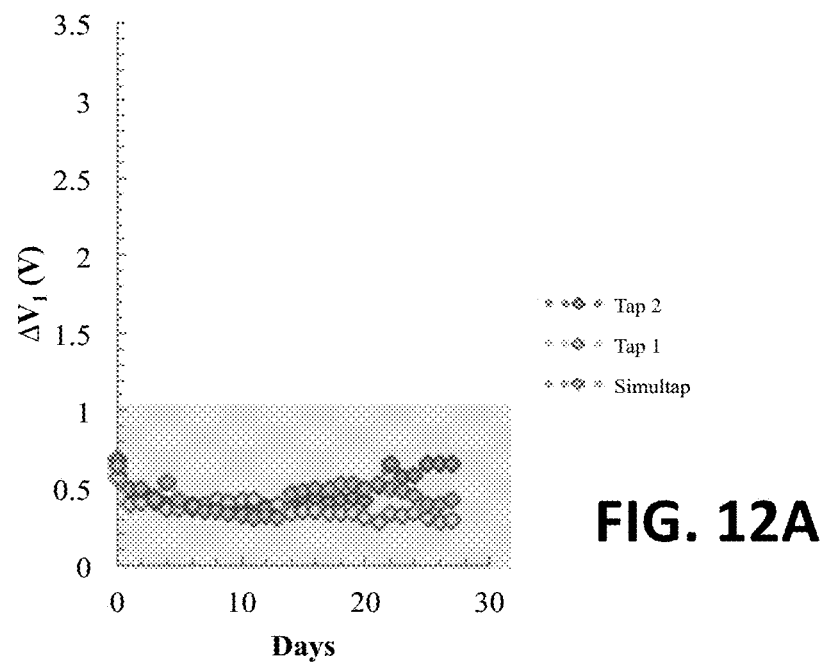

FIG. 12A shows an original $\Delta V_1$ reading at an anode of an exemplary four-electrode sensor in Tap 1, Tap 2, and Simultap for four weeks.

Figure 12B:
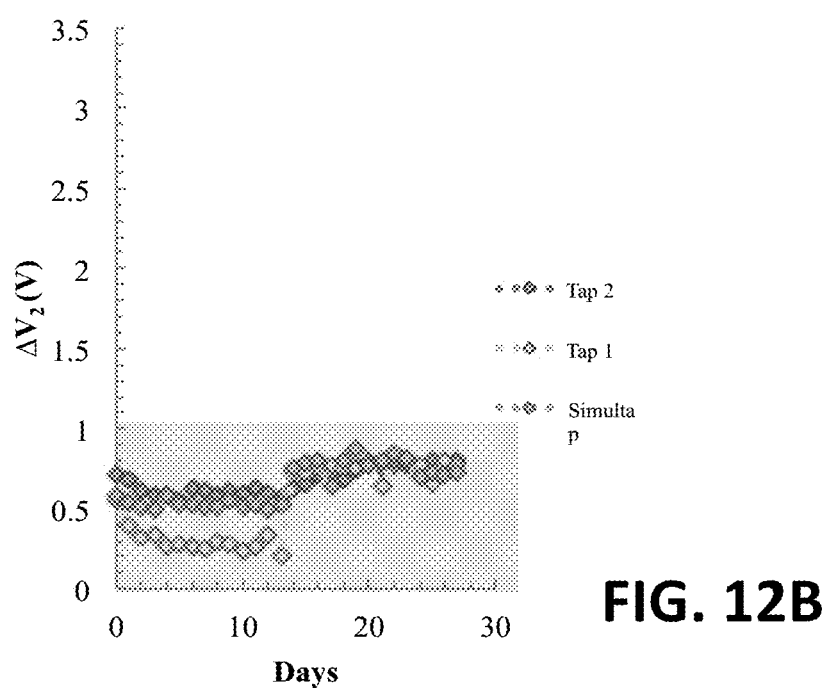

FIG. 12B shows an original $\Delta V_2$ reading at a cathode of an exemplary four-electrode sensor in Tap 1, Tap 2, and Simultap for four weeks.

Figure 13A:
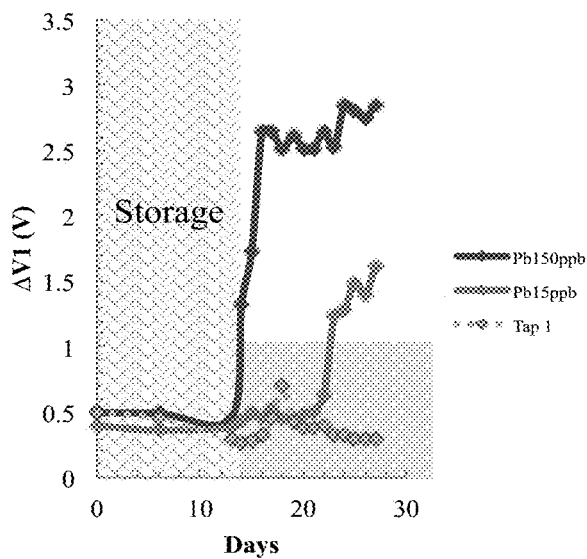

FIG. 13A shows an anode side of an exemplary four-electrode sensor stored in Tap 1, 15 ppb, and 150 ppb solutions for two weeks. The four-electrode sensor functioned normally after the two weeks.

Figure 13B:
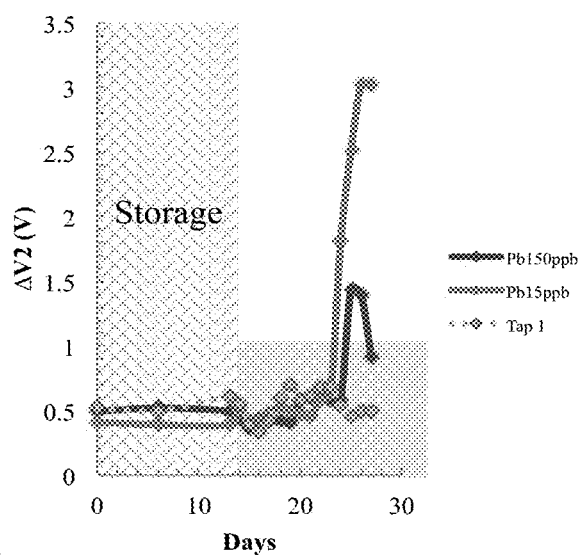

FIG. 13B shows a cathode side of an exemplary four-electrode sensor stored in Tap 1, 15 ppb, and 150 ppb solutions for two weeks. The four-electrode sensor functioned normally after the two weeks.

Figure 13C:
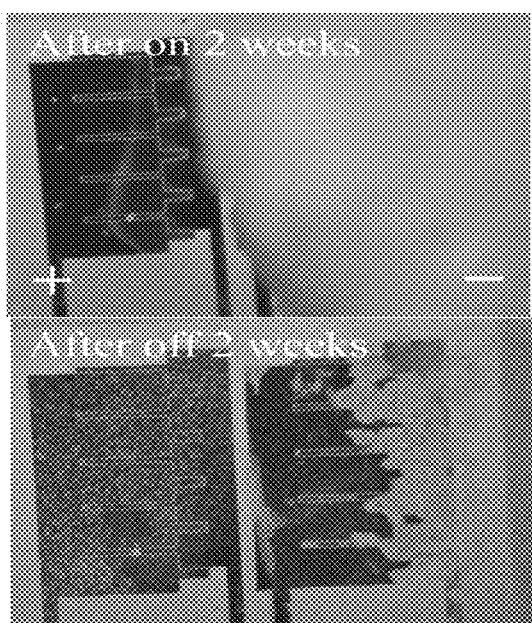

FIG. 13C shows photographs of an exemplary four-electrode sensor. The photographs show that hardness precipitated on a cathode side after the sensor was turned on for two weeks, but mostly dissolved again after the sensor was off for another two weeks.

Figure 13D:
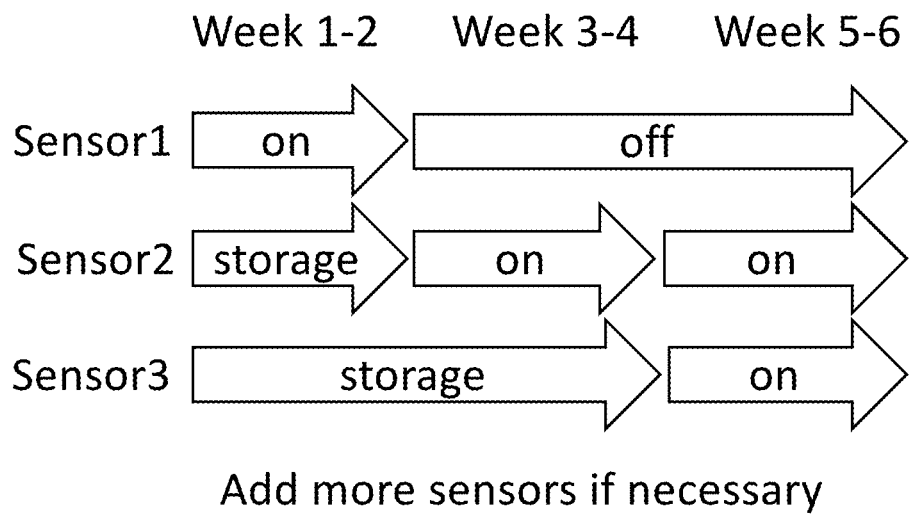

FIG. 13D shows a first exemplary approach for using a four-electrode sensor for long-term monitoring. Here, multiple sensors are in a single water pipe.

Figure 13E:
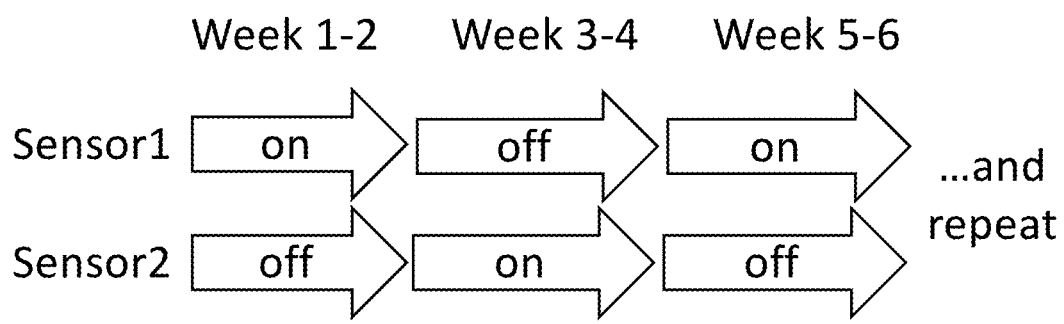

FIG. 13E shows a second exemplary approach for using a four-electrode sensor for long-term monitoring. Here, two electrodes are being used alternatively.

Corresponding reference numerals indicate corresponding parts throughout the several views of the drawings.

DETAILED DESCRIPTION

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term "comprising," is to be understood as a non-restrictive term used to describe and claim various embodiments set forth herein, in certain aspects, the term may alternatively be understood to instead be a more limiting and restrictive term, such as "consisting of" or "consisting essentially of." Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of "consisting of," the alternative embodiment excludes any additional compositions, materials, components, elements, features, integers, operations, and/or process steps, while in the case of "consisting essentially of," any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Any method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

When a component, element, or layer is referred to as being "on," "engaged to," "connected to," or "coupled to" another element or layer, it may be directly on, engaged, connected or coupled to the other component, element, or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Spatially or temporally relative terms, such as "before," "after," "inner," "outer," "beneath," "below," "lower," "above," "upper," and the like, may be used herein for ease of description to describe one element or feature's relationship to another element(s) or feature(s) as illustrated in the figures. Spatially or temporally relative terms may be intended to encompass different orientations of the device or system in use or operation in addition to the orientation depicted in the figures.

Throughout this disclosure, the numerical values represent approximate measures or limits to ranges to encompass minor deviations from the given values and embodiments having about the value mentioned as well as those having exactly the value mentioned. All numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters.

In addition, disclosure of ranges includes disclosure of all values and further divided ranges within the entire range, including endpoints and sub-ranges given for the ranges. As referred to herein, ranges are, unless specified otherwise, inclusive of endpoints and include disclosure of all distinct values and further divided ranges within the entire range. Thus, for example, a range of "from A to B" or "from about A to about B" is inclusive of A and of B.

Example embodiments will now be described more fully with reference to the accompanying drawings.

The sensor for detecting metal, such as lead, in water advantageously has a long lifetime so that the sensor can be inserted into a water pipe for years until lead leakage happens. Advantageously, the sensor can automatically inform users, without regular examination. Sensor that are affordable would enable most families to have one installed, for example, at each end point of their water service lines. Accordingly, the current technology provides sensors that can be made in efficient and inexpensive processes that are only about the size of a rice grain (less than or equal to about 1 mm$^3$, not including a power source). The small size of the sensors allows them to be inserted in pipes, and they require only simple circuits and, readily available power sources, for example, two AAA batteries for operation by way of anon-limiting example. The sensors may be made with inert platinum electrodes and are suitable for long-term water monitoring of heavy metals. None-limiting examples of heavy metals include heavy metals include lead (Pb), zinc (Zn), copper (Cu), iron (Fe), antimony (Sb), arsenic (As), cadmium (Cd), chromium (Cr), mercury (Hg), nickel (Ni), selenium (Se), thallium (Ti), silver (Ag), manganese (Mn), barium (Ba), and combinations thereof.

Figure 1:
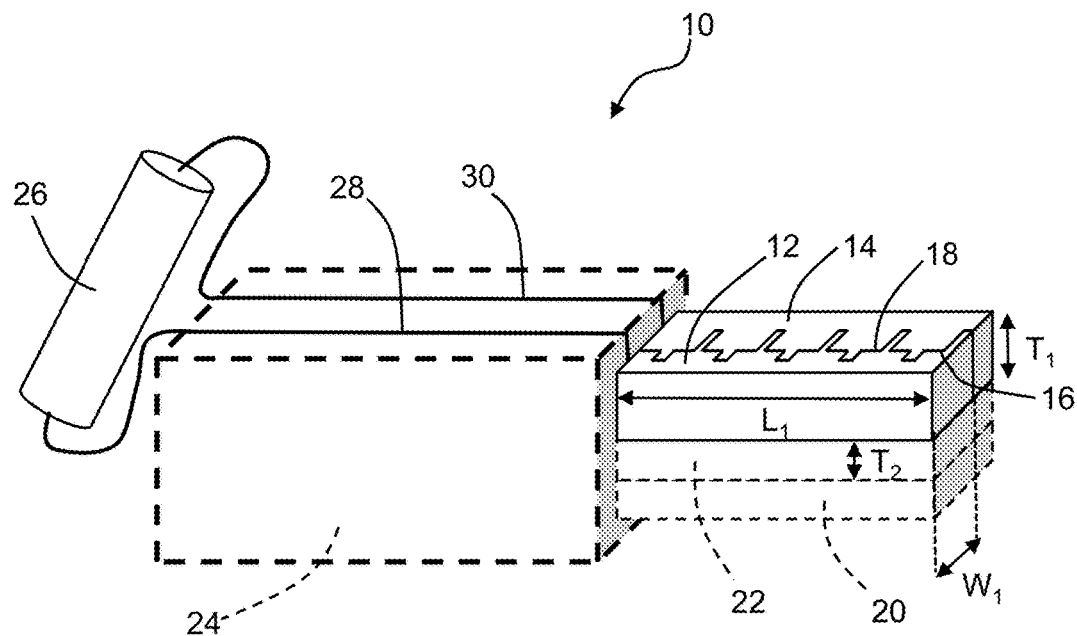
FIG. 1 is an illustration of a two-electrode sensor according to various aspects of the current technology.

FIG. 1 shows a two-electrode sensor 10 according to various aspects of the current technology. The two-electrode sensor 10 comprises a first electrode 12 and a second electrode 14. In various embodiments, the four-electrode sensor 100 is free of a reference electrode or a ligand. The first electrode 12 comprises a first surface 16 that defines a first pattern and the second electrode 14 comprises a second surface 18 that defines a second pattern. The first and second patterns are complementary, i.e., as mirror images or negatives, to each other, such they fit together, leaving a gap or path therebetween. For example, the first surface 16 and the second surface 18 are separated from each other by a gap having a distance of greater than or equal to about 500 nm to less than or equal to about 10 μm, greater than or equal to about 750 nm to less than or equal to about 8 μm, or greater than or equal to about 1 urn to less than or equal to about 5 μm. The gap distance is substantially constant, i.e., deviates by less than about 20% of an average distance. In some embodiments, the distance is about 1 μm, about 2 μm, about 3 μm, about 4 μm, about 5 μm, about 6 μm, about 7 μm, about 8 μm, about 9 μm, or about 10 μm.

The designs of the first and second patterns are not limited, other than that they are complementary to each other. For example, the first pattern can comprise at last one peak and at least one valley, wherein the at least one peak and the at least one valley are individually squared, flat, curved, or pointed. Accordingly, in various aspects of the current technology, the first and second patterns comprise a plurality of complementary complex peaks and valleys. Put another way, the first and second electrodes 12, 14 have complementary interdigitated (and complex) surfaces that are separated from each other by the gap.

The first electrode 12 is a positive electrode and the second electrode 14 is a negative electrode, and each electrode 12, 14 comprises a conductive metal. However, it is understood that the charge of the electrodes 12, 14 can be switched. Non-limiting examples of conductive metals include platinum, gold, silver, copper, and combinations thereof. The first and second electrodes 12, 14 have a length Li of greater than or equal to about 500 μm to less than or equal to about 2 mm, a width Wi of greater than or equal to about 50 μm to less than or equal to about 1 mm, and a thickness $T_1$ of greater than or equal to about 250 Å to less than or equal to about 2000 Å. Moreover, the first electrode 12 has a surface area of greater than or equal to about 0.4 mm$^2$ to less than or equal to about 0.5 mm$^2$ and the second electrode 14 has a surface area of greater than or equal to about 0.3 mm$^2$ to less than or equal to about 0.4 mm$^2$. The first and second electrodes 12, 14 are also characterized by a contact length to surface area ratio of from greater than or equal to about 5 cm$^{-1}$ to less than or equal to about 20 cm$^{-1}$, wherein the contact length is the distance between the electrodes. However, it is understood that the dimensions of the first and second electrodes 12, 14 can be scaled up or scaled down, depending on conditions in which the two-electrode sensor 10 will be used. For example, the dimensions may be scaled down when the two-electrode sensor 10 is inserted into a small water pipe or scaled up when the two-electrode sensor 10 is inserted into a large water pipe.

As shown in FIG. 1, the first and second electrode 12, 14 are optionally coupled to a substrate 20 by way of an adhesive layer 22 disposed between the first and second electrodes 12, 14 and the substrate 20. The optional adhesive layer 22 has a thickness $T_2$ of greater than or equal to about 50 nm to less than or equal to about 500 nm. The substrate is crystalline or amorphous and comprises silicon dioxide (glass) or any other material known in the art. The adhesive layer 22 comprises, as non-limiting examples, titanium, chromium, or a combination thereof. Additionally, the first and second electrodes 12, 14 are optionally coupled to a solid support 24. The solid support 24 comprises a non-conductive material, such as, for example, a polymer, such as a plastic, a glass, or a printed circuit (PC) board.

The first electrode 12 and the second electrode 14 are connected to a power source 26, for example, by a first lead 28 and a second lead 30, respectively. The first and second leads 28, 30 are wires, circuits printed on a circuit board, or a combination thereof. The power source 26 is not limited, and can be, for example, a battery, a plurality of batteries, a photovoltaic device, or an electrical service of a building, such as a home.

The two-electrode sensor 10 is configured to detect heavy metals in water without incorporating a reference electrode or a ligand. For example, when the two-electrode sensor 10 contact water comprising heavy metals, such as lead (Pb), zinc (Zn), copper (Cu), iron (Fe), antimony (Sb), arsenic (As), cadmium (Cd), chromium (Cr), mercury (Hg), nickel (Ni), selenium (Se), thallium ($T_1$), silver (Ag), manganese (Mn), barium (Ba), and combinations thereof, as non-limiting examples, and when an electric potential is applied between the first and second electrodes 12, 14, lead is oxidized in lead dioxide and deposited at the first electrode 12 and the other metals are reduced and deposited at the second electrode 14. A change in voltage relative to a baseline value obtained in the absence of detectable heavy metals, indicates the presence of heavy metals. The two-electrode sensor 10 indirectly quantifies a heavy metal concentration in that the shorter the time between operating the sensor and recording a voltage change, i.e., the shorting of the electrodes, the higher the concentration of the heavy metal.

Figure 2:
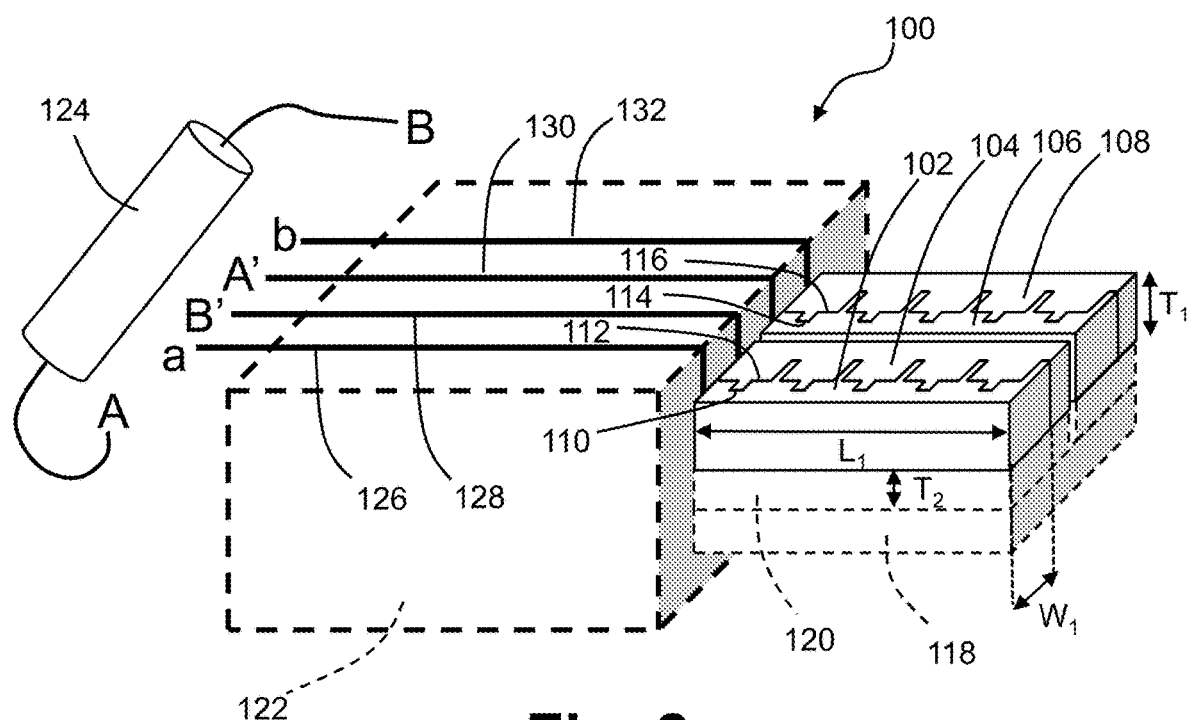
FIG. 2 is an illustration of a four-electrode sensor according to various aspects of the current technology.

FIG. 2 shows a four-electrode sensor 100 according to various aspects of the current technology. The four-electrode sensor 100 is similar to the two-electrode sensor 10 shown in FIG. 1, but with a pair of first and second electrodes 12, 14. More particularly, the four-electrode sensor 100 comprises a first electrode 102, a second electrode 104, a third electrode 106, and a fourth electrode 108. In various embodiments, the four-electrode sensor 100 is free of a reference electrode and a ligand. The first electrode 102 comprises a first surface 110 that defines a first pattern, the second electrode 104 comprises a second surface 112 that defines a second pattern, the third electrode 106 comprises a third surface 114 that defines a third pattern, and the fourth electrode 108 comprises a fourth surface 116 that defines a fourth pattern. The first and second patterns, and the third and fourth patterns, are complementary, i.e., as mirror images or negatives, to each other, such they fit together, leaving a gap or path therebetween. For example, the first surface 110 and the second surface 112, and the third surface 114 and the fourth surface 116, are separated from each other by individual gaps having a distance of greater than or equal to about 500 nm to less than or equal to about 10 μm, greater than or equal to about 750 nm to less than or equal to about 8 µm, or greater than or equal to about 1 µm to less than or equal to about 5 µm. The gap distance is substantially constant, i.e., deviates by less than about 20% of an average distance. In some embodiments, the gap distance is about 1 µm, about 2 µm, about 3 µm, about 4 µm, about 5 µm, about 6 µm, about 7 µm, about 8 µm, about 9 µm, or about 10 µm. Also, the second electrode 104 and the third electrode 106 are separated from each other by a distance of greater than or equal to about 1 µm to less than or equal to about 500 µm, such as by a distance of about 10 µm, about 20 µm, about 30 µm, about 40 µm, about 50 µm, about 60 µm, about 70 µm, about 80 µm, about 90 µm, about 100 µm, about 250 µm, or about 500 µm.

The designs of the first, second, third and fourth patterns are not limited, other than that the first and second patterns are complementary to each other and the third and fourth patterns are complementary to each other. For example, the first or third pattern can comprise at last one peak and at least one valley, wherein the at least one peak and the at least one valley are individually squared, flat, curved or pointed. Accordingly, in various aspects of the current technology, the first and second patterns comprise a plurality of complementary complex peaks and valleys and the third and fourth patterns comprise a plurality of complementary peaks and valleys. Put another way, the first and second electrodes 102, 104 have complementary interdigitated surfaces 110, 112 that are separated from each other by the first gap and the third and fourth electrodes 106, 108 have complementary (and complex) interdigitated surfaces 114, 116 that are separated from each other by the second gap.

In electroplating operation mode, the first electrode 102 is a positive electrode and the fourth electrode 108 is a negative electrode. However, it is understood that the charge of the electrodes 102, 108 can be switched. Each of the first, second, third, and fourth electrodes 102, 104, 106, 108 comprises a conductive metal as described above in regard to FIG. 1. The first, second, third, and fourth electrodes 102, 104, 106, 108 have a length Li of greater than or equal to about 500 µm to less than or equal to about 2 mm, a width Wi of greater than or equal to about 50 µm to less than or equal to about 1 mm, and a thickness $T_1$ of greater than or equal to about 250 Å to less than or equal to about 2000 Å. Moreover, the first electrode 102 has a surface area of greater than or equal to about 0.4 mm$^2$ to less than or equal to about 0.5 mm$^2$, the second electrode 104 has a surface area of greater than or equal to about 0.4 mm$^2$ to less than or equal to about 0.5 mm$^2$, the third electrode 106 has a surface area of greater than or equal to about 0.1 mm$^2$ to less than or equal to about 0.3 mm$^2$, and the fourth electrode 108 has a surface area of greater than or equal to about 0.3 mm$^2$ to less than or equal to about 0.4 mm$^2$. The first, second, third, and fourth electrodes 102, 104, 106, 108 are also characterized by a contact length to surface area ratio of from greater than or equal to about 5 cm$^{-1}$ to less than or equal to about 20 cm$^{-1}$. However, it is understood that the dimensions of the first, second, third, and fourth electrodes 102, 104, 106, 108 can be scaled up or scaled down, depending on conditions in which the four-electrode sensor 100 will be used. For example, the dimensions may be scaled down when the four-electrode sensor 100 is inserted into a small water pipe or scaled up when the four-electrode sensor 100 is inserted into a large water pipe.

As shown in FIG. 2, the first, second, third, and fourth electrodes 102, 104, 106, 108 are optionally coupled to a substrate 118 by way of an adhesive layer 120 disposed between the first, second, third, and fourth electrodes 102, 104, 106, 108 and the substrate 118. The optional adhesive layer 120 has a thickness $T_2$ of greater than or equal to about 50 nm to less than or equal to about 500 nm. The substrate 118 is crystalline or amorphous and comprises silicon dioxide (glass) or any other material known in the art. The adhesive layer 120 comprises, as non-limiting examples, titanium, chromium, or a combination thereof. Additionally, the first, second, third, and fourth electrodes 102, 104, 106, 108 are optionally coupled to a solid support 122. The solid support 122 comprises a non-conductive material, such as, for example, a polymer, such as a plastic, a glass, or a printed circuit (PC) board.

The first, second, third, and fourth electrodes 102, 104, 106, 108 are electrically connected to a first lead 126, a second lead 128, a third lead 130, and a fourth lead 132, respectively. Moreover, the first, second, third, and fourth leads 126, 128, 130, 132 are independently and individually connectable to a power source 124. Put another way, the sensor 100 is configured such that the first, second, third, and fourth leads 126, 128, 130, 132 can be individually coupled to and decoupled from the power source 124. The first, second, third, and fourth leads 28, 30 are wires, circuits printed on a circuit board, or a combination thereof. The power source 124 is not limited, and can be, for example, a battery, a plurality of batteries, a photovoltaic device, or an electrical service of a building, such as a home. The power source 124 has a connectable end A and a second connectable end B. The first lead 126 has a connectable end a, the second lead 128 has a connectable end B', the third lead has a connectable end A', and the fourth lead 132 has a connectable end b. Each of the connectable ends a, B', A', and b can be individually and reversibly electronically connected to connected ends A and B of the battery 124. For example, when an electric potential is applied the first and fourth electrodes 102, 108 via an aA-Bb connection, heavy metals are electroplated on either the second or third electrode 104, 106 depending on the standard reduction potential of individual heavy metals.

The four-electrode sensor 100 is configured to selectively detect lead in water without incorporating a reference electrode or a ligand. For example, the four-electrode sensor 100 is placed in an environment wherein it contacts water comprising heavy metals, such as lead (Pb), zinc (Zn), copper (Cu), iron (Fe), antimony (Sb), arsenic (As), cadmium (Cd), chromium (Cr), mercury (Hg), nickel (Ni), selenium (Se), thallium (Ti), silver (Ag), manganese (Mn), barium (Ba), and combinations thereof, as non-limiting examples. When the electrode 100 is connected in an aA-Bb configuration, an electric potential (sufficient to reduce lead ions to lead oxide) is applied between the first and fourth electrodes 102, 108, lead is oxidized into lead dioxide, and the lead dioxide is electroplated onto the second electrode 104. In various embodiments, 1.5 V is applied. Meanwhile the remaining heavy metals are reduced and electroplated onto the third electrode 106. When the electrode is then connected in an aA-BB' configuration, an electric potential is applied between the first and second electrodes 102, 104. A change in voltage relative to a baseline measurement when the electrode 100 is disposed in water that does not contain detectable levels of lead, signifies that lead is present in the water. When the electrode is then connected in an A'A-Bb configuration, an electric potential is applied between the third and fourth electrodes 106, 108. A change in voltage relative to a baseline measurement when the electrode 100 is disposed in water that does not contain detectable levels of heavy metals signifies that heavy metals other than lead are present in the water. Although not shown in FIG. 2, in various embodiments the four-electrode sensor 100 comprises an alert feature that provides at least one of an audible and visual alert when at least one of lead or another heaving metal is detected in water. The four-electrode sensor 100 indirectly quantifies a heavy metal concentration in that the shorter the time between operating the sensor and recording a voltage change, i.e., the shorting of the electrodes, the higher the concentration of the heavy metal.

Accordingly, the current technology also provides as water pipe having an internal bore section through which water flows, wherein the four-electrode sensor 100 is disposed within the internal bore section.

The current technology further provides a method for fabricating the two-electrode sensor 10 shown in FIG. 1 or the four-electrode sensor 100 shown in FIG. 2. The method comprises disposing an adhesive layer on a substrate; disposing a photoresist onto the adhesive layer; and disposing a photoresist mask on the photoresist. The photoresist mask comprises a pattern defining either the first and second electrode 12, 14 of the two-electrode sensor 10 of FIG. 1 or the first, second, third, and fourth electrodes 102, 104, 106, 108 of the four-electrode sensor 100 of FIG. 2. As a non-limiting example, the pattern can define a first electrode and a second electrode, the first electrode and the second electrode having complementary surfaces that are separated from each other by a distance of greater than or equal to about 500 nm to less than or equal to about 10 µm; a third electrode and a fourth electrode, the third electrode and the fourth electrode having complementary surfaces that are separated from each other by a distance of greater than or equal to about 500 nm to less than or equal to about 10 µm; wherein the second electrode and the third electrode are separated from each other by a distance of greater than or equal to about 1 µm to less than or equal to about 1 mm.

The method then comprises transferring the pattern of the photoresist mask into the adhesive layer to generate a patterned adhesive layer; and disposing a layer of a conductive material onto the patterned adhesive layer. Each of the substrate, the adhesive layer, and the conductive material are described above.

The current technology also provides a method for continuously monitoring a water sample for the presence of heavy metals. In certain variations, heavy metals include, e.g., in the water sample, lead (Pb), zinc (Zn), copper (Cu), iron (Fe), antimony (Sb), arsenic (As), cadmium (Cd), chromium (Cr), mercury (Hg), nickel (Ni), selenium (Se), thallium (Ti), silver (Ag), manganese (Mn), barium (Ba), and combinations thereof. In certain preferred aspects, the heavy metal is lead (Pb). The method comprises contacting a sensor with the water sample. The water sample can be contained in a vessel. The vessel is non-limited and can be, for example, a pipe or a container, such as a glass or a pitcher. The pipe can be, for example, a water pipe in a building, such as a house, apartment, condominium, office, or commercial building. The sensor can be any sensor described above. In various aspects of the current technology, the sensor comprises a first electrode and a second electrode, the first electrode and the second electrode having complementary interdigitated surfaces that are separated from each other by a first gap having a first distance of greater than or equal to about 500 nm to less than or equal to about 10 µm, and a third electrode and a fourth electrode, the third electrode and the fourth electrode having complimentary complementary interdigitated surfaces that are separated from each other by a second gap having a second distance of greater than or equal to about 500 nm to less than or equal to about 10 µm. The second electrode and the third electrode are separated from each other by a distance of greater than or equal to about 1 µm to less than or equal to about 1 mm. In various embodiments, the sensor is the four-electrode sensor 100 described in FIG. 2. In various embodiments, the method is free of using a reference electrode or ligands.

The method also comprises applying a first electrical potential between the first and fourth electrodes. The first electrical potential causes the oxidation of lead (Pb) to lead dioxide ($PbO_2$), which electroplates on the second electrode. The first electrical potential also causes the reduction of other heavy metals, which electroplate on the third electrode.

The method then comprises applying a second electrical potential between the first and second electrodes, and measuring a first voltage between the first and second electrodes. The first voltage is compared to a baseline voltage in water that does not contain detectable levels of lead. Therefore, the method comprises determining that lead is present in the water when the first voltage is different from a baseline voltage in water that does not contain detectable levels of lead. In some embodiments, the method includes generating an alert when the first voltage is different from a baseline voltage in water that does not contain detectable levels of lead. The alert can be at least one of an audible and a visual alert.

In some embodiments, the method further comprises, after the measuring a first voltage between the first and second electrodes, applying a third electrical potential between the third and fourth electrodes, and measuring a second voltage between the third and fourth electrodes. The second voltage is compared to a baseline voltage in water that does not contain detectable levels of heavy metals other than lead. Therefore, the method comprises determining that heavy metals other than lead are present in the water when the second voltage is different from a baseline voltage in water that does not contain detectable levels heavy metals other than lead. In some embodiments, the method includes generating an alert when the second voltage is different from a baseline voltage in water that does not contain detectable levels of heavy metals. The alert can be at least one of an audible and a visual alert.

Embodiments of the present technology are further illustrated through the following non-limiting examples.

Example 1

Leakage of lead and other heavy metals into drinking water is a significant health risk and one that is not easily detected. Simple sensors containing only platinum electrodes for the detection of heavy metal contamination in drinking water are now described. A two-electrode sensor can identify the existence of a variety of heavy metals in drinking water, and a four-electrode sensor can distinguish lead from other heavy metals in solution. No false-positive response is generated when the sensors are placed in simulated and actual tap water contaminated by heavy metals. Lead detection on the four-electrode sensor is not affected by the presence of common ions in tap water. Experimental results suggest that the sensors can be embedded in water service lines for long periods of time until lead or other heavy metals are detected. With its low cost (~$0.10/sensor) and long-term operation, the sensors are ideal for heavy metal detection of drinking water.

Methods

Fabrication of Electrodes.

Sensors (FIGS. 3A-3B) is constructed using physical vapor deposition of 300/1000 Å Ti/Pt on a 500 μm thick, 4 inch diameter glass wafer. Pressure is controlled under $2 \times 10^{-6}$ Torr with a deposition rate of 15 and 5 Å/s, respectively. The sensors are integrated with a PC board as shown in FIG. 3A. A two-electrode system is shown in FIG. 3B, and the electrodes are separated with a 5 or 10 μm gap. A four-electrode sensor is fabricated by the same method but in a different geometry as shown in FIG. 4A. Small gaps between left two electrodes and right two electrodes are 5 μm, and a large gap between the middle two electrodes is 50 μm.

Experiment Setup and the Measurement of the Impedances.

In FIG. 3C, an integrated two-electrode sensor is connected with two AAA batteries and a 100 kΩ resistor. The sensor is dipped in 100 ml test solution in a beaker. The voltage difference across a resistor, ΔV, is measured by Labview as the signal. ΔV reflects the overall impedance across the electrodes: ΔV increases when the impedance across the two electrodes decreases. All solutions are changed every week during the experiments. The schematic diagram of the four-electrode system is shown in FIG. 4B. The sensor is connected with two AAA batteries and a 100 kΩ resistance. When the sensor is operated and electroplating metals, the sensor is connected as aA-Bb. Voltage difference across the resistor is measured as $\Delta V_1$ when the sensor is reconnected as aA-BB' to measure impedance between the anode and the second electrode. When the sensor is reconnected as A'A-Bb, the voltage difference across the resistor is measured as $\Delta V_2$ to detect the impedance between the cathode and the third electrode.

Test Solutions.

Simulated test solutions are made with $PbCl_2$, $CuCl_2$, $ZnCl_2$, and $FeCl_2$ in $10^{-2}$ M NaCl made with DI water. The NaCl is added to increase the conductivity of the solution to about 1000 μS/cm, the upper limit of drinking water set by EPA. The composition of the simulated tap water (Simultap) and Ann Arbor tap water (information gathered from annual Ann Arbor water quality reports 2003-2015) is listed in Table 1. Simultap contains relatively higher concentrations of common ions relative to real tap water. The real sample Tap 1 and Tap 2 are collected in Ann Arbor, Mich., USA. The heavy metals in the real tap water samples are examined with ICPMS and listed in Table 2. The lead concentration is tested both by ICPMS in a University of Michigan and National testing laboratory approved by the EPA. Tap 1 contains no lead and relatively low concentration of all heavy metals. Tap 2 contains about 5 ppb of lead, which is smaller than action level (15 ppb), and 0.7 mg/L of copper, which is relatively high but smaller than SMCL. $PbCl_2$ is added in Tap 1 to make the "Tap 1+Pb 150 ppb" sample but no extra NaCl was added.

TABLE 1

Ion concentration in simulated tap water (Simultap) and real Ann Arbor, MI tap water.

| Ion | Simultap (mg/L) | Ann Arbor (mg/L) |
|---|---|---|
| $Na^+$ | 270 | 48-67 |
| $K^+$ | 11 | — |
| $Mg^{2+}$ | 71 | 10-33 |
| $Ca^{2+}$ | 46 | 23-66 |
| $HCO_3^-$ | 61 | — |
| $CO_3^{2-}$ | 14 | 100-176 |
| $NO_3^-$ | 18 | 0-0.06 |
| $SO_4^{2-}$ | 390 | 41-82 |
| $Cl^-$ | 364 | 98-147 |

TABLE 2

Concentration of heavy metals ions in tap water samples and EPA regulation.

| Metal | Unit | Tap 1 | Tap 2 | EPA regulations | Notes |
|---|---|---|---|---|---|
| Pb (NL) | ppb | ND | 3.0 | 0 (MCL); 15 (AL) | NL: National Testing laboratory |
| Pb | ppb | ND | 5.0 | 0 (MCL); 15 (AL) | ND: Not detectable (<1 ppb) |
| Cu | mg/L | 0.004 | 0.70 | 1.3 (MCL); 1.0 (SMCL) | MCL: Maximum contaminant level |
| Zn | mg/L | 0.004 | 0.59 | 5.0 (SMCL) | SMCL: Secondary maximum contaminant level |
| Fe | mg/L | 0.003 | 0.033 | 0.3 (SMCL) | AL: Action Level |
| Al | mg/L | 0.024 | 0.012 | 0.050-0.2 (SMCL) | |
| Cr | mg/L | 0.0002 | 0.0004 | 0.1 (SMCL) | |
| Mn | mg/L | 0.0001 | 0.005 | 0.05 (SMCL) | |

Auger Spectroscopy.

Auger spectroscopy data is collected for the specimens on a PHI 680 Auger nanoprobe that is equipped with a field emission electron gun and a cylindrical mirror energy analyzer (energy resolution $\Delta E/E \approx 0.25\%$). A base pressure of the test chamber is about $1.2 \times 10^{-9}$ torr. The native oxidized layer of the chromium pellet is removed by Ar ion sputtering. To avoid the charging effect of insulating samples under electron beam irradiation, Pb oxides powder with size less than 3 μm is pressed into a tin foil or a carbon type so that a high energy electron beam can penetrate these lead oxide particles, while "devices" are placed on the tilt stage in order to reduce the embedded charging effect caused by the deep penetration of incident electron beams. A small electron beam current of 1 nA is used to irradiate the specimens.

Results and Discussion

Simple sensors for detecting heavy metal in drinking water are achieved with simple platinum electrodes. When the electrodes are connected with 2 AAA batteries (~3.2V), heavy metal ions are reduced to conductive metals on the cathode. As shown in Table 3, the electric resistances of reduced metals are 9 to 10 orders of magnitude smaller than drinking water. Thus, when reduced metals connect the gap between the electrodes, the impedance across the electrodes drops significantly. The impedance change is an indicator of the existence of heavy metals in the water.

TABLE 3

Resistivity of reduced and oxidized metals and drinking water.

| Oxidized metal | Resistivity (Ω · m) | Reduced metal | Resistivity (Ω · m) |
|---|---|---|---|
| $PbO_2$ | $2\text{-}74 \times 10^{-6}$ | Pb | $2.20 \times 10^{-7}$ |
| ZnO | >2.2 | Zn | $5.90 \times 10^{-8}$ |
| CuO | 25-100 | Cu | $1.68 \times 10^{-8}$ |

TABLE 3-continued

Resistivity of reduced and oxidized metals and drinking water.

| Oxidized metal | Resistivity ($\Omega \cdot m$) | Reduced metal | Resistivity ($\Omega \cdot m$) |
|---|---|---|---|
| $Cu_2O$ | $10^2$-$10^4$ | | |
| $Fe(OH)_3/FeO(OH)/Fe(OH)_2/Fe_2O_3$ | $10^3$-$10^6$ | Fe | $1.00 \times 10^{-7}$ |
| Drinking water | 10-2000 | — | — |

Two-Electrodes System

A two-electrode sensor with 5 µm gaps can detect lead ions at a level of 15 ppb with no false responses. The performance of the 5 µm gap, two-electrodes system is shown in FIG. 5A and a 10 µm gap sensor in FIG. 5B. For both sensors, $\Delta V$ increases significantly and becomes greater than 1V within two days in 150 ppb $Pb^{2+}$ solution. The growth of $\Delta V$ represents conductive layers formed between the two electrodes; thus, reducing the impedance. The sensor with a 5 µm gap shows a response ($\Delta V$ greater than 1V) in 15 ppb $Pb^{2+}$ (action level) solution in three days, but the sensor with 10 µm gap shows no response throughout the two weeks experiment. These results suggest that a 5 µm gap between the electrodes is more sensitive than a larger gap. Both sensors have no false positive response from Simultap, showing common ions in water did not generate conductive species.

The two-electrodes sensor with 5 µm gap shows a response to almost all solutions with heavy metals and shows no false positive responses. The sensor is tested in various simulated solutions designed to mimic the EPA heavy metal regulations listed in Table 2, and the performance is plotted in FIG. 5C. $\Delta V$ increases in all heavy metal solutions but remains the same in Simultap, which contains no heavy metal ions. The variation of $\Delta V$ is because some conductive deposition may fall off during the two-week experiment, and the time $\Delta V$ remains greater than 1V is not crucial. The sensor is also tested in two real tap water samples and a mixture of real tap water and lead. The performance in both the simulated and real samples is shown in Table 4. The solutions with lead higher than the action level, and solutions with no heavy metal ions, are listed. The sensor shows fast response (<3 days) to lead, zinc, and copper solutions. No false positive response was generated in either Simultap or Tap 1.

TABLE 4

Two-electrode sensor performance in different solutions.

| | Solution | Response day (days) | Max $\Delta V$ (V) |
|---|---|---|---|
| Simulated sample | Pb 150 ppb | 3 | 2.25 |
| | Pb 15 ppb | 3 | 1.89 |
| | Fe 6.0 mg/L | 9 | 1.00 |
| | Fe 0.3 mg/L | 13 | 1.01 |
| | Zn 5.0 mg/L | 2 | 1.25 |
| | Zn 0.5 mg/L | 3 | 1.27 |
| | Cu 1.0 mg/L | 2 | 3.15 |
| | Cu 0.1 mg/L | 1 | 3.20 |
| | Simultap | — | 0.4 |
| Real sample | Tap 1 | — | 0.8 |
| | Tap 1 + Pb 150 ppb | 1 | 1.65 |
| | Tap 1 + Pb 15 ppb | — | 0.60 |
| | Tap 2 | 8 | 1.60 |

However, the responses in simulated ferrous solution and the mixture of real tap water and lead ions are slower than expected. The sensor generates a slow and weak response (max $\Delta V$=1V at 9th day) in simulated ferrous solutions even at very high concentrations (20 times larger than SMCL). For the same 15 ppb Pb concentration, the sensor responds in 3 days in 15 ppb Pb solution but does not respond to the mixture of Tap 1+15 ppb Pb. The sensor also responds more slowly to Tap 2 (0.7 mg/L Cu) than 0.1 mg/L Cu solution.

Operation of the Sensor

The performance of the sensor can be explained with the help of FIG. 6. The sensor shows a response only if conductive deposition connects the gap and thus decreases the impedance between electrodes. The tendency of metal ions reducing to conductive metal can be represented by the standard reduction potentials, $E^0$. The higher the $E^0$, the easier the ions can be reduced. $E^0$ values of common metal ions in contaminated drinking water are listed in Table 5. $E^0_{acid}$ is the $E^0$ in acid (pH=0) and $E^0$ basic is the value in basic (pH=14) conditions. $Pb^{2+}$, $Zn^{2+}$, $Fe^{2+}$, and $Cu^{2+}$ can be reduced to conductive metals when the potential on the cathode is smaller than −0.76. With 2 AAA batteries, the potential on the cathode is sufficient to reduce the heavy metal ions.

TABLE 5

Standard potential $E^0$ of metal ions in drinking water.

| Reaction | $E^0$acid (V) | $E^0$basic (V) |
|---|---|---|
| $PbO_2/Pb^{2+}$ | 1.46 | — |
| $O_2/H_2O$ | 1.23 | — |
| $Pt_2+/Pt$ | 1.18 | — |
| $Fe^{3+}/Fe^{2+}$ | 0.77 | — |
| $Cu^+/Cu$ | 0.52 | — |
| $Cu^{2+}/Cu$ | 0.34 | — |
| $PbO_2/Pb(OH)_2$ | — | 0.25 |
| $H^+/H_2$ | 0.00 | −0.83 |
| $Pb^{2+}/Pb$ | −0.13 | — |
| $Fe^{2+}/Fe$ | −0.44 | — |
| $Zn^{2+}/Zn$ | −0.76 | — |

Lead ions are the only ions that can deposit a conductive species around the anode. The dominant reaction around the anode is oxidation, and lead is the only element that can be oxidized into a conductive species, i.e., lead dioxide. Generation of lead dioxide is possible because the $E^0$ of $PbO_2/Pb^{2+}$ is 1.46V (Table 5). Lead dioxide is considered conductive because its resistivity is about six to eight orders of magnitude smaller than drinking water and the other oxidized metals (Table 3).

No false positive response is possible from typical ions in tap water.

Concentrations of major ions in Ann Arbor, Mich., tap water are listed in Table 1 as an example. Though the concentrations of ions vary from location to location, the species are mostly the same. The standard reduction potentials of these ions are listed in Table 6. Unless the cathode potential is smaller than −2.3V (which is 1.4V smaller than the potential required to reduce the heavy metals), no conductive species are likely to deposit on the sensor surface and drop the impedance. With 2 AAA batteries, false positive responses are not likely.

TABLE 6

Standard potential $E^0$ of major ions in drinking water.

| Reaction | $E^0_{acid}$ (V) | $E^0_{basic}$ (V) |
|---|---|---|
| $Cl_2/Cl^-$ | 1.40 | 1.36 |
| $O_2/H_2O$ | 1.23 | — |
| $NO_3^-/NO_2$ | 0.94 | — |
| $SO_4^{2-}/S$ | 0.35 | — |
| $H^+/H_2$ | 0.00 | −0.83 |
| $NO_3^-/NH_3$ | — | −0.12 |
| $CO_3^{2-}/CH_4$ | — | −0.73 |
| $SO_4^{2-}/SO_3^{2-}$ | — | −0.94 |
| $Mg^{2+}/Mg$ | −2.36 | — |
| $Na^+/Na$ | −2.72 | −2.72 |
| $K^+/K$ | −2.94 | −2.94 |
| $Ca^{2+}/Ca$ | −2.87 | — |

Though false positive responses are unlikely, the performance of the two-electrode sensor may be delayed by precipitated hardness and rust. The solubility of water hardness, which is white with the major component being calcium carbonate, decreases with increasing pH. With 2 AAA batteries (~3.2V), the sensor electrolyzes water during operation. Thus the local pH around the anode is acidic and basic around the cathode. Hardness precipitates on the cathode, blocking the gap between the electrodes, and delaying the sensor response. Rust, which is mostly ferric and ferrous oxide, is another precipitation that is possible due to altered pH. Though $E^0$ suggests ferric and ferrous ions are possible to be reduced into iron, previous research shows the ions may instead precipitate as rust. The ability of the sensor to detect iron is thus lower than the ability to detect other metals, so the sensor showed weaker and slower response in ferrous solution than in other heavy metal solutions.

FIG. 7 shows pictures of the sensors operated in different test solutions and corroborates the hypothesis described above. Lead is the only element deposited on the anode (+) while zinc and copper are reduced on the cathode (−). Simultap precipitates white hardness, and iron solutions precipitates red rust. Thus, the two-electrode sensor is ideal for heavy metal detection but does not distinguish lead from other heavy metals. Lead is the most toxic metal in drinking water and should be identified for the safety of the users.

Four-Electrode System

To distinguish the most toxic element, lead, from other heavy metals, a four-electrode sensor is designed and tested. Two extra electrodes are placed between the cathode and the anode as shown in FIGS. 4A and 4B. The small gap between the left two electrodes and the right two electrodes is 5 μm. The large gap between the middle two electrodes is 50 μm. As explained previously, lead ions are the only ions that will deposit a conductive species around the anode while other heavy metals can still deposit on the cathode. The four-electrode sensor thus contains both a lead detector and a heavy metal sensor.

The expected reactions in the four-electrode system are illustrated in FIG. 8. Lead ions oxidize to lead dioxide around the anode and connects the gap between the anode and the second electrode. At the cathode, other metals are reduced, and hardness and rust precipitate due to pH change. Because lead is the only ion that can be oxidized to a conductive species in the system, lead is the only element that deposits a conductive compound around the anode. The two electrodes on the left are thus lead detectors and the two electrodes on the right are other heavy metal sensors.

The concept is confirmed with experiment results and had no false positive response on both sides in simulated and real tap water. The original reading of the four-electrode system are shown in FIGS. 9A and 9B. Both $\Delta V_1$ and $\Delta V_2$ maintains less than 1V in Simultap and Tap 1. $\Delta V_1$ increases significantly in both $Pb^{2+}$ solutions, and shows no false positive response to high concentrations of zinc and iron. $\Delta V_2$ detects the existence of all other heavy metals and increases significantly in $Zn^{2+}$, $Cu^{2+}$, and $Fe^{2+}$ solutions. $\Delta V_2$ does not respond in 15 ppb $Pb^{2+}$ because the low ion concentration and most of $Pb^{2+}$ is oxidized on the anode.

One downside is that copper, which is also a toxic metal regulated by EPA MCLs, can generate a false response on the lead detector. A late response (12th day) on $\Delta V_1$ appears in the 1 mg/L copper solution. This response occurs because copper is the easiest ion to be reduced among the four metal ions ($Cu^{2+}/Cu$ is 0.34 V as listed in Table 5). On the anode, oxidations are the major reactions and few reductions happen due to the forced electrical current. However, both oxidation and reduction are possible on the middle two floating electrodes, which means that copper could be reduced on these two electrodes as well. When copper is reduced on the second electrode, the anode and the electrode may be connected. The impedance between these two electrodes drops significantly, $\Delta V_1$ increases, and a false positive is generated.

The lead detection using the four-electrode sensor can occur without being influenced by the main ions in the tap water. Table 7 lists the performance of the four-electrode sensor in various solutions. The solutions with lead levels higher than the action level, and solutions with no heavy metal ions, are listed. The lead sensor detects all solutions with lead levels above the action level though the low concentration (5 ppb) of lead in Tap 2 is not detected. The ability for lead detection is not influenced by the major ions in the solution. Since the hardness is precipitated around the cathode due to pH change and it is not blocking the lead detector, the response days for the action level sample "15 ppb Pb" is the same with the real tap water sample "Tap 1+Pb 15 ppb". On the other hand, the heavy metal sensor is delayed by the harness precipitated around the cathode. For the same concentration of lead, copper, and zinc, the sensor detects much faster (1 days) in a simulated solution than in the mixture of heavy metals and real tap water. The heavy metal detector also shows no response to Tap 2, which contains a relatively high concentration of copper (0.7 mg/L).

TABLE 7

Four-electrode sensor performance in different solutions.

| | Solution | $\Delta V_1$ Anode Response day (days) | $\Delta V_1$ Anode Max $\Delta V$ (V) | $\Delta V_2$ Cathode Response day (days) | $\Delta V_2$ Cathode Max $\Delta V$ (V) |
|---|---|---|---|---|---|
| Simulated | Pb 150 ppb | 1 | 3.1 | 5 | 2.76 |
| | Pb 15 ppb | 7 | 2.72 | — | 0.76 |
| | Fe 6.0 mg/L | — | 0.89 | 10 | 3.19 |
| | Zn 5.0 mg/L | — | 0.67 | 3 | 3.22 |
| | Zn 0.5 mg/L | — | 0.61 | 3 | 3.12 |
| | Cu 1.0 mg/L | 12 | 1.86 | 1 | 3.13 |
| | Cu 0.1 mg/L | — | 0.44 | 2 | 3.07 |
| | Pb 15ppb + Cu 1 mg/L + Zn 5 mg/L | 2 | 2.99 | 1 | 3.21 |
| | Simultap | — | 0.31 | — | 0.59 |

TABLE 7-continued

Four-electrode sensor performance in different solutions.

| | Solution | $\Delta V_1$ Anode Response day (days) | $\Delta V_1$ Anode Max $\Delta V$ (V) | $\Delta V_2$ Cathode Response day (days) | $\Delta V_2$ Cathode Max $\Delta V$ (V) |
|---|---|---|---|---|---|
| Real sample | Tap 1 | — | 0.57 | — | 0.71 |
| | Tap 2 | — | 0.69 | — | 0.7 |
| | Tap 1 + Pb 150 ppb | 2 | 3.05 | — | 0.56 |
| | Tap 1 + Pb 15 ppb | 7 | 2.14 | 12 | 2.4 |
| | Tap 1 + Pb 15 ppb + Cu 1 mg/L + Zn 5 mg/L | 9 | 1.36 | 5 | 3.02 |

Validation with Auger Spectroscopy

The compositions of the metal depositions on the anode and cathode are confirmed by using Auger electron spectroscopy (AES). AES is a surface-sensitive characterization technique based on the analysis of energetic electrons emitted from an excited atom after a series of internal relaxation events. The energy position and shape of an Auger peak contains a significant amount of information about the chemical environment of the source ion. This chemical information results from the dependence of the atomic energy levels, the loss structure, and the valence band structure on the local bonding. Compared to the high and slowly changing backscattered electron background, the Auger peaks usually look small. Commonly, the first order derivatives of the spectra are employed to highlight chemical changes.

The chemical states of the lead deposition on the anode can be validated by comparing the kinetic energy of the valence band Auger electrons. In the experiment, 99.99% Pb and 99.999% PbO are purchased from Sigma Aldrich and used as validation standards. Pb02 is the sensor anode operated in 150 ppb Pb solution for two weeks and Pb002 is in 15 ppb. As seen from FIG. 10A (inset), electron beam excited Pb ONN Auger transitions shows a high sensitivity to the chemical states. The metallic Pb ONN Auger electrons (98.0 eV) have higher kinetic energies than those of PbO (87.6 eV) and the specimen (86.5 eV). Similar observations also occur at Pb MNV transitions (1800-2300 eV) in the raw data (FIG. 10A). The kinetic energy of the Auger electron depends only on the energy levels involved, however, not on the energy of the primary excitation. These energy levels relate to the type of atom and the chemical environment in which the atom is located. The energy levels are element specific, so that the Auger electrons emitted by the sample carry information about their chemical composition. The resulting spectra are used to determine the identity of the emitting atoms and some information about their environment. Basically, the inner shell energy levels are much less affected by the chemical states, so the kinetic energy of the valence band Auger electrons can directly reflect the chemical states of the source ions.

Another approach to validate the chemical status is the Auger peak intensities, and with the NOO positions it can be concluded that the deposition on the anode had $PbO_2$. The Auger peak intensities are determined by the ionization cross section, Auger yield possibility, the mean escape depth and the backscattering factor. It is quite difficult to individually quantify these factors. Usually, the intensity (peak-to-valley height) of AES peaks can be simplified to the product of a sensitivity factor and the concentration of the element. Based on the sensitivity factors for O and Pb elements derived from the standard PbO, the atomic concentration ratio of the specimens can be calculated from their peak-to-valley heights (see Table 8). By combining the peak Pb NOO position it can be concluded that the deposition in 15 ppb Pb solution is mainly $PbO_2$ while a mixture of $PbO_2$, PbO, and Pb in 150 ppb solution.

TABLE 8

The averaged atomic ratio obtained from AES data of selected spots. The errors for all elements are estimated to be 5%.

| Specimen | C | O | Pb | Zn | Cu | Na | Cl | O/Pb |
|---|---|---|---|---|---|---|---|---|
| Pb standard | — | — | 100.0 | — | — | | | |
| PbO standard | 31.3 | 34.4 | 34.3 | — | — | | | 1.0 |
| Pb02 (150 ppb) | 15.4 | 37.9 | 22.8 | — | — | 11.9 | 11.8 | 1.7 |
| Pb002 (15 ppb) | 55.2 | 17.2 | 8.4 | — | — | 10.2 | 10.1 | 2.1 |
| Pb 15 ppb + Cu 1 mg/L + Zn 5 mg/L (anode +) | 30.5 | 45.4 | 29.1 | — | — | — | — | 1.6 |
| Pb 15 ppb + Cu 1 mg/L + Zn 5 mg/L (cathode −) | 15.5 | 34.4 | — | 40.9 | 6.8 | — | — | |

As seen from FIG. 10B, when the sensor operates in the mixed solution (Pb 15 ppb+Cu 1 mg/L+Zn 5 mg/L), most Pb deposites on the anode while Cu and Zn deposites on the cathode. No Pb (or a trace amount of Pb) deposites on the cathode confirming that the sensor has high elemental selectivity. The atomic ratios are listed in Table 8, which are the average of 5 different spots in order to provide the reproducibility. The errors for all elements are estimated to be 5%.

The electron-excited Auger electron spectroscopy also provides very high spatial resolution (about 10 nm), which makes it especially suitable for small feature analysis and elemental mapping. The Pb distribution of sample Pb02 (the sensor in 150 ppb for two weeks) is mapped using Pb NOO and MNV Auger transition peaks, is displayed in FIGS. 11A-11C. The left-up side is the anode while the right-down side is the second electrode. As indicated by the higher concentration of lead between the electrodes, the lead deposited between and connected the electrodes.

Long-Term Monitoring of the Four-Electrode Sensor

Heavy metals can leak into water without of the awareness of users and thus one of the most important features of heavy metal sensors is continuous long-term monitoring. To achieve this goal, the sensor needs to be stored or operated in solution for long periods of time and still function normally. The sensors discussed here are ideal for such operation because the inert electrodes provide no lifetime limitation. As shown in FIGS. 12A and 12B, both sides of the sensor perform well in Simultap, Tap 1, and Tap 2 after the sensor is operated continuously for four weeks. The sensor also functions normally after storage in solution for two weeks, as shown in FIGS. 13A and 13B. In Tap 1, 15 ppb Pb, and 150 ppb Pb solution, the impedances of the sensor on both sides remains substantially constant during storage (immersed in the solution without any supplied voltage) and the sensor functions normally after activation. $\Delta V_1$ on the lead detection side increases significantly (greater than 1V) in both 15 ppb and 150 ppb lead solutions but both $\Delta V_1$ and $\Delta V_2$ remain less than 1V in tap water. In FIG. 13C, the sensor is operated (on) in Tap 1 for two weeks and then stored (off) in Tap 1 for another two weeks. Hardness precipitates on the cathode during operation mostly dissolved after the storage, thus both the lead detector and the other heavy metal sensors remain unblocked and the sensor can be used again.

These experiments suggest that long-term monitoring is possible using two methods. The first approach, as shown in FIG. 13D, is to put multiple electrode combinations on a single sensor. The surface area of the sensor is less than 1 mm², but duplicate sensors can easily be constructed on this or slightly larger formats. If necessary, wax or other materials can be applied to the sensors during storage to protect the sensor's surface. The materials can be easily removed just before operation with embedded Ti/Pt heaters to melt and remove the material. The other approach, as shown in FIG. 13E, is to alternate two sensors. One sensor operates for two weeks while the other is immersed in the same solution with no applied power. The alternation of the sensors can be programmed and operated automatically, and the sensors without applied power will regenerate through dissolution of precipitated ions.

The response day for 15 ppb Pb solution in FIG. 7 is 7 days but 9 days after turned on in FIG. 13C. Therefore, for water safety monitoring, real-time detection of the action level of lead or other dangerous heavy medals is extremely important, and quantification of that level can occur, for example, off-line.

During long-term monitoring, water temperature influence on the sensor is negligible. For example, lead is the only element that can possible be oxidized to a conductive species no matter what the water temperature is. Also, the dominant redox reactions will not be changed by water temperature in a residential range (10-50° C.). Water temperature does not alter the qualification ability of the sensor. Notwithstanding, the hardness solubility decreases with increasing water temperature. For example, the solubility of calcium carbonate changes from 0.53 mM at 25° C. to 0.35 mM at 50° C. Therefore, more hardness may precipitate onto the cathode side at 50° C., but the lead-detecting anode is not influenced due to the pH difference.

The current technology provides sensors that are suitable for long-term monitoring of lead in drinking water. It is noted that response time can be shortened by it changing the sensor geometry. The sensing method of the sensor is to grow reduced metal or lead dioxide bridges between electrodes in order to change the impedance. Thus by increasing the bridge-formation possibility, the response time is decreased. Some designs cause the majority of heavy metal ions to deposit on the electrodes instead of between the gap. To increase the bridge-formation by metal ions and shorten the response time, the length-to-surface-area ratio and be increased or the gap distance between the electrodes can be decreased.

The sensor provided by various aspects of the present disclosure can detect contamination of lead or other heavy metals in a variety of applications. The four-electrode sensor detects lead on the left two electrodes and detect other heavy metals on the right two electrodes. The inert platinum electrode and the experimental results indicate the sensor has a long lifetime, and the sensor can be easily inserted in pipes for continuous monitoring and detection. The sensor can perform excellent qualification, which is important in the monitoring of lead contamination. Toxic lead exposure causing permanent injuries through contaminated tap water has been a concern in the US, and the current sensor is a solution for detecting such lead outbreaks.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A sensor for detecting a heavy metal in water, the sensor comprising:
a first electrode and a second electrode, the first electrode and the second electrode having complementary interdigitated surfaces that are separated from each other by a gap having a distance of greater than or equal to about 500 nm to less than or equal to about 10 μm;
first and second leads connected to the first electrode and the second electrode, respectively, the first and second leads being configured to connect the first and second electrodes to a power source; and
a resistance connected to the first lead such that a voltage difference across the resistance is indicative of an impedance between the first and second electrodes;
wherein the sensor is configured to continuously monitor the water for the heavy metal by detecting an increase in the voltage difference arising from a change in the impedance due to electroplating of a conductive species of the heavy metal on the first electrode or the second electrode.

2. The sensor according to claim 1, wherein the first electrode has a surface area of greater than or equal to about 0.4 mm² to less than or equal to about 0.5 mm² and the second electrode has a surface area of greater than or equal to about 0.3 mm² to less than or equal to about 0.4 mm².

3. The sensor according to claim 1, further comprising:
a third electrode and a fourth electrode, the third electrode and the fourth electrode having complementary interdigitated surfaces that are separated from each other by a distance of greater than or equal to about 500 nm to less than or equal to about 10 μm,
wherein the second electrode and the third electrode are separated from each other by a gap having a distance of greater than or equal to about 1 μm to less than or equal to about 1 mm.

4. The sensor according to claim 3, wherein the first electrode is a positive electrode and the fourth electrode is a negative electrode.

5. The sensor according to claim 3, further comprising:
a third lead electrically connected to the third electrode; and
a fourth lead electrically connected to the fourth electrode;
wherein the sensor is configured such that the first, second, third and fourth leads can be individually coupled to and decoupled from the power source.

6. The sensor according to claim 1, further comprising one or more batteries as the power source.

7. The sensor according to claim 1, wherein the heavy metal is lead.

8. The sensor according to claim 1, wherein the sensor is free of a reference electrode and a ligand.

9. The sensor according to claim 1, further comprising:
a substrate to which the first and second electrodes are coupled.

10. The sensor according to claim 9, wherein the substrate comprises glass.

11. A water pipe having an internal bore section through which water flows, wherein the electrode according to claim 1 is disposed within the internal bore section.

12. The sensor according to claim 1, wherein the electroplating of the first electrode or the second electrode connects the gap between the first and second electrodes such that the impedance decreases.

13. The sensor according to claim 1, wherein the power source provides an electrical potential sufficient to oxidize the heavy metal in the water into the conductive species on the first or second electrode.

14. The sensor according to claim 13, wherein the heavy metal is lead and the conductive species is lead dioxide.

15. The sensor according to claim 1, wherein one of the first and second electrodes is connected to the power source as an anode such that lead in the water is oxidized to form lead dioxide on the anode.

16. The sensor according to claim 1, further comprising a printed circuit board to which the first and second electrodes are coupled.

17. The sensor according to claim 1, wherein each of the first and second electrodes comprises platinum.

18. The sensor according to claim 1, wherein the resistance comprises a resistor.

19. The system according to claim 18, wherein, in the lead (Pb) sensing configuration, the system is configured to detect an increase in the voltage difference arising from a change in the impedance between the first pair of electrodes due to electroplating of lead dioxide on the electrode of the first pair of electrodes connected to the power source during the electroplating mode.

20. The system according to claim 18, wherein, in the heavy metal sensing configuration, the system is configured to detect an increase in the voltage difference arising from a change in the impedance between the second pair of electrodes due to electroplating of a heavy metal conductive species on the electrode of the second pair of electrodes connected to the power source during the electroplating mode.

21. The system according to claim 18, wherein the heavy metal sensing configuration is configured to detect copper reduced on the electrode of the second pair of electrodes connected to the power source during the electroplating mode.

22. A system for detecting heavy metals in water, the system comprising:
    a power source;
    a resistance connected to the power source;
    a lead (Pb) sensor comprising a first pair of electrodes and a first pair of leads to connect respective electrodes of the first pair of electrodes to the power source via the resistance, the first pair of electrodes having complementary interdigitated surfaces that are separated from each other by a gap in a range from about 500 nm to about 10 μm;
    a heavy metal sensor comprising a second pair of electrodes and a second pair of leads to connect respective electrodes of the second pair of electrodes to the power source via the resistance, the second pair of electrodes having complementary interdigitated surfaces that are separated from each other by a gap in a range from about 500 nm to about 10 μm;
    wherein the system is operable in an electroplating mode in which one of the first pair of electrodes and one of the second pair of electrodes are connected to the power source;
    wherein the system is further operable in a lead (Pb) sensing configuration when the first pair of electrodes are connected to the power source such that a voltage difference across the resistance is indicative of an impedance between the first pair of electrodes; and
    wherein the system is further configurable in a heavy metal sensing configuration when the second pair of electrodes are connected to the power source such that a voltage difference across the resistance is indicative of an impedance between the second pair of electrodes.

* * * * *